United States Patent
Sazuka et al.

(10) Patent No.: US 12,236,149 B2
(45) Date of Patent: Feb. 25, 2025

(54) INFORMATION PROCESSING SYSTEM DISPLAYING EMOTIONAL INFORMATION

(71) Applicant: SONY GROUP CORPORATION, Tokyo (JP)

(72) Inventors: Naoya Sazuka, Tokyo (JP); Koki Katsumata, Tokyo (JP)

(73) Assignee: SONY GROUP CORPORATION, Tokyo (JP)

(*) Notice: Subject to any disclaimer, the term of this patent is extended or adjusted under 35 U.S.C. 154(b) by 0 days.

(21) Appl. No.: 18/550,980

(22) PCT Filed: Feb. 25, 2022

(86) PCT No.: PCT/JP2022/008063
§ 371 (c)(1),
(2) Date: Sep. 18, 2023

(87) PCT Pub. No.: WO2022/209499
PCT Pub. Date: Oct. 6, 2022

(65) Prior Publication Data
US 2024/0176569 A1 May 30, 2024

(30) Foreign Application Priority Data

Mar. 29, 2021 (JP) .................. 2021-056032
Aug. 17, 2021 (JP) .................. 2021-132938

(51) Int. Cl.
*G06F 3/14* (2006.01)
*A61B 5/00* (2006.01)
(Continued)

(52) U.S. Cl.
CPC ............. *G06F 3/14* (2013.01); *A61B 5/165* (2013.01); *A61B 5/4803* (2013.01);
(Continued)

(58) Field of Classification Search
CPC ..... A61B 5/742; A61B 5/7275; A61B 5/4803; A61B 5/165; A61B 5/7455; G06F 3/14; G06F 3/012
See application file for complete search history.

(56) References Cited

U.S. PATENT DOCUMENTS

2013/0300645 A1* 11/2013 Fedorov .................. G06F 3/01
345/156
2017/0340258 A1* 11/2017 Zou ..................... A61B 5/6898
(Continued)

FOREIGN PATENT DOCUMENTS

JP  2005-198828 A  7/2005
JP  2019-029984 A  2/2019
(Continued)

OTHER PUBLICATIONS

Wang, et al., "EEG-Based Emotion Recognition Using Frequency Domain Features and Support Vector Machines", 18th International conference on neural information processing, researchgate, Nov. 13-17, 2011, 11 pages.
(Continued)

*Primary Examiner* — Abbas I Abdulselam
(74) *Attorney, Agent, or Firm* — CHIP LAW GROUP

(57) ABSTRACT

Provided is an information processing system that includes an estimation section and a display section. The estimation section estimates emotional information about a target living body on the basis of at least one of biological information or
(Continued)

motion information about the target living body acquired by a sensor. The display section displays the emotional information on a display surface.

17 Claims, 21 Drawing Sheets

(51) Int. Cl.
  *A61B 5/16* (2006.01)
  *G06F 3/01* (2006.01)
  *G10L 15/22* (2006.01)
  *G10L 25/63* (2013.01)
  *G06V 40/16* (2022.01)

(52) U.S. Cl.
  CPC .......... *A61B 5/7275* (2013.01); *A61B 5/742* (2013.01); *A61B 5/7455* (2013.01); *G06F 3/012* (2013.01); *G10L 15/22* (2013.01); *G10L 25/63* (2013.01); *G06F 3/013* (2013.01); *G06F 3/015* (2013.01); *G06F 2203/011* (2013.01); *G06V 40/174* (2022.01)

(56) References Cited

U.S. PATENT DOCUMENTS

| 2019/0336724 | A1* | 11/2019 | Li | A61B 5/165 |
| 2020/0060603 | A1* | 2/2020 | Bower | A61B 5/167 |
| 2020/0357303 | A1* | 11/2020 | Zhang | G09B 21/006 |

FOREIGN PATENT DOCUMENTS

| JP | 2020-035344 A | 3/2020 |
| JP | 2020-203058 A | 12/2020 |
| WO | 2016/170810 A1 | 10/2016 |
| WO | 2020/116280 A1 | 6/2020 |

OTHER PUBLICATIONS

Zhai, et al., "Realization of stress detection using psychophysiological signals for improvement of human-computer interactions", Proceedings IEEE SoutheastCon, Apr. 8, 2005, pp. 415-420.

Veltman, et al., "Physiological indices of workload in a simulated flight task", Biological Psychology, vol. 42, No. 3, Feb. 5, 1996, pp. 323-342.

Appelhans, et al., "Heart rate variability as an index of regulated emotional responding", Review of general psychology, vol. 10, No. 3, Sep. 2006, pp. 229-240.

Lam, et al., "Emotion regulation and cortisol reactivity to a social-evaluative speech task", Psychoneuroendocrinology, vol. 34, No. 9, ScienceDirect, Oct. 1, 2009, pp. 1355-1362.

Lyons, et al., "Automatic classification of single facial images", IEEE transactions on pattern analysis and machine intelligence, vol. 21, No. 12, Dec. 1999, pp. 1357-1362.

Chen, et al., "Automatic classification of eye activity for cognitive load measurement with emotion interference", Computer Methods and Programs in Biomedicine, vol. 110, No. 2, May 1, 2013, pp. 111-124.

Zhang, et al., "Respiration-based emotion recognition with deep learning", Computers in Industry, vols. 92-93, Nov. 2017, pp. 84-90.

Nakanishi, et al., "Facial skin temperature decreases in infants with joyful expression", Infant Behavior and Development, vol. 31, No. 1, Jan. 2008, pp. 137-144.

Choi, et al., "Evaluation of Fear Using Nonintrusive Measurement of Multimodal Sensors", Sensors, vol. 15, No. 7, Jul. 20, 2015, pp. 17507-17533.

Paul Ekman, "Facial action coding system", URL: https://www.paulekman.com/facial-action-coding-system/, 1977.

International Search Report and Written Opinion of PCT Application No. PCT/JP2022/008063, issued on May 24, 2022, 15 pages of ISRWO.

\* cited by examiner

[ FIG. 1 ]
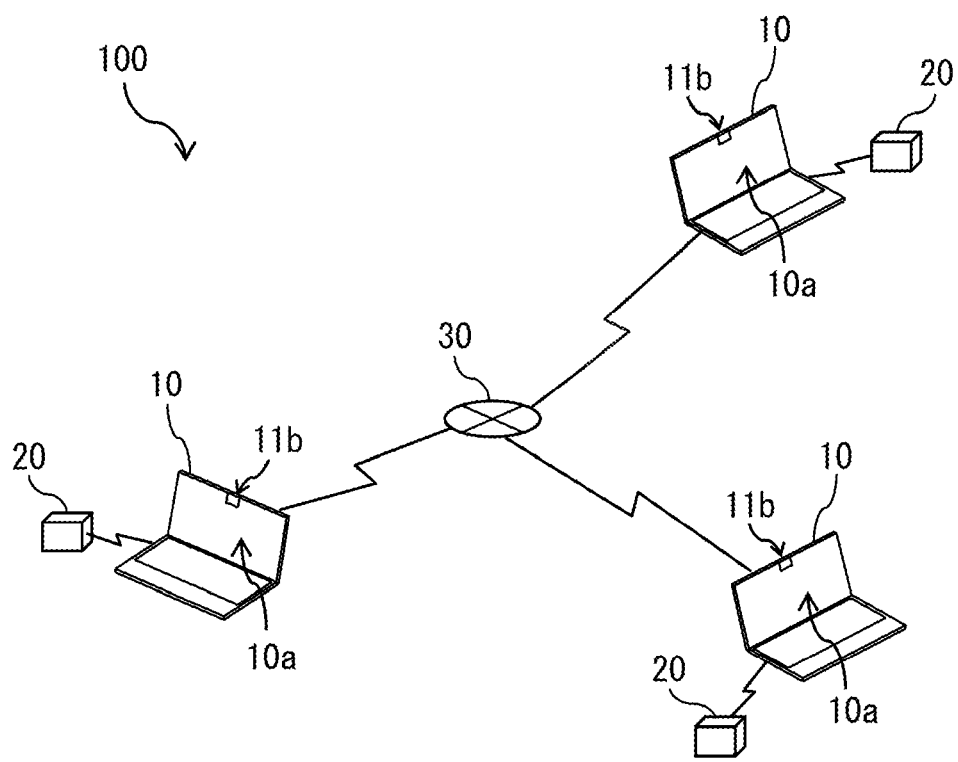

[ FIG. 2 ]
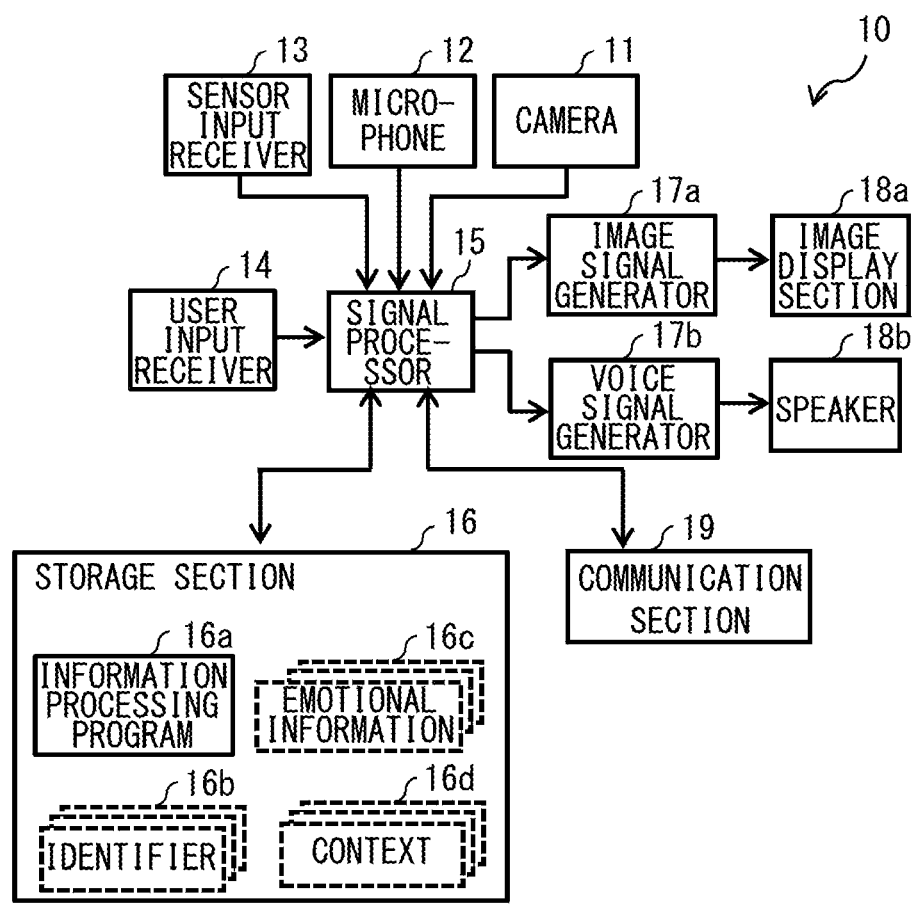

[ FIG. 3 ]
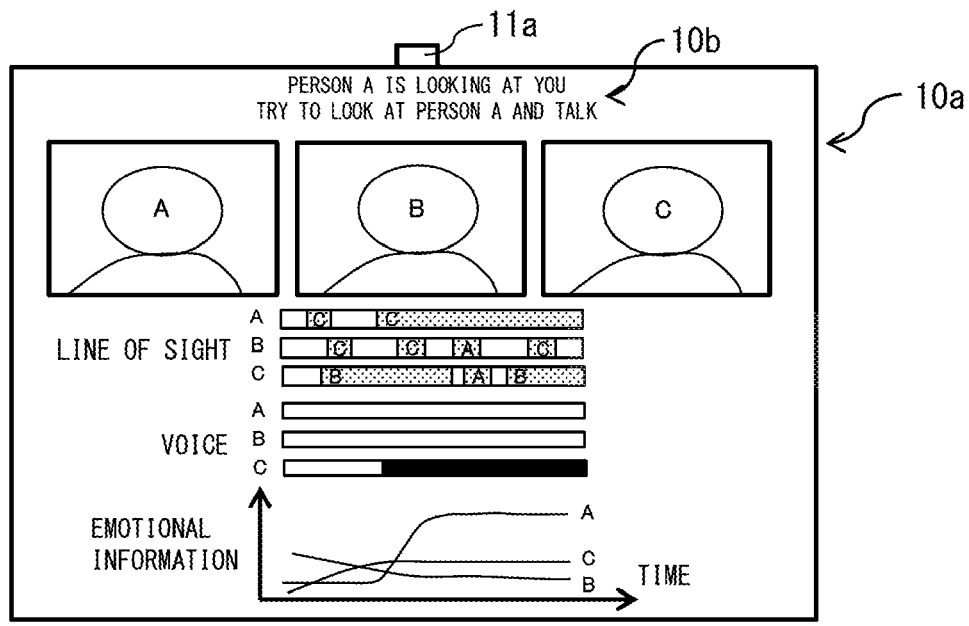
[ FIG. 4 ]
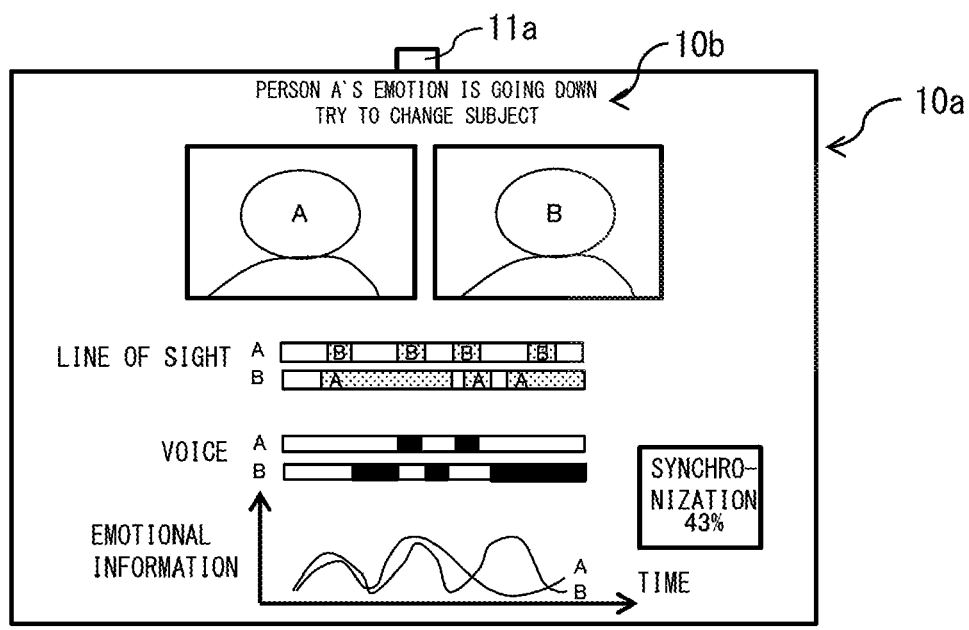

[ FIG. 5 ]
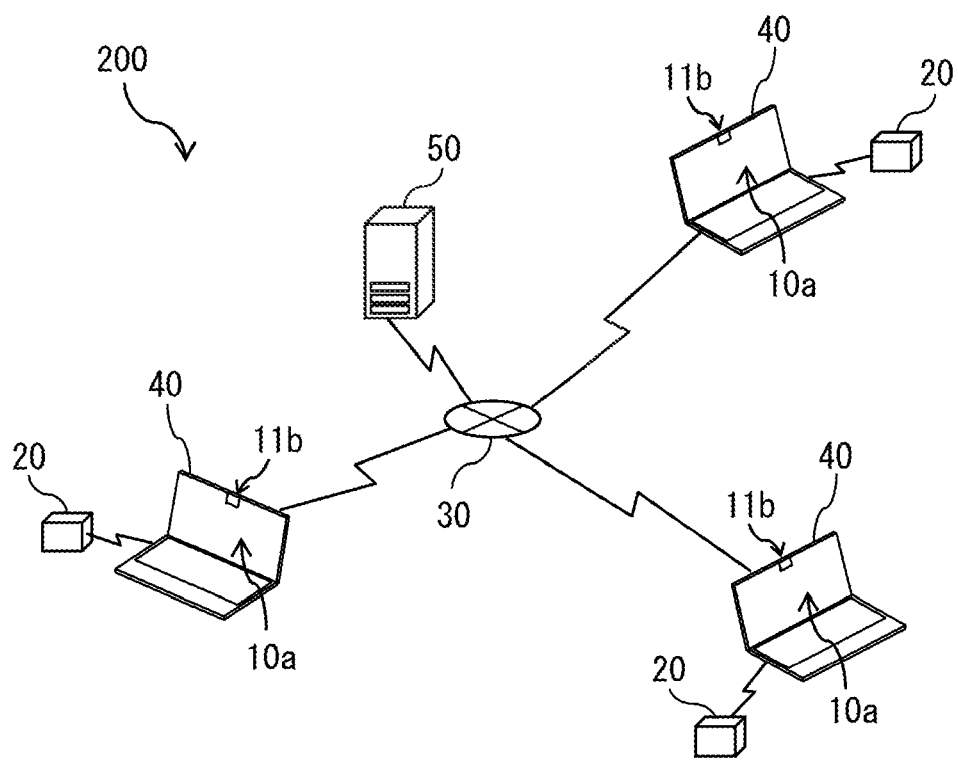

[ FIG. 6 ]
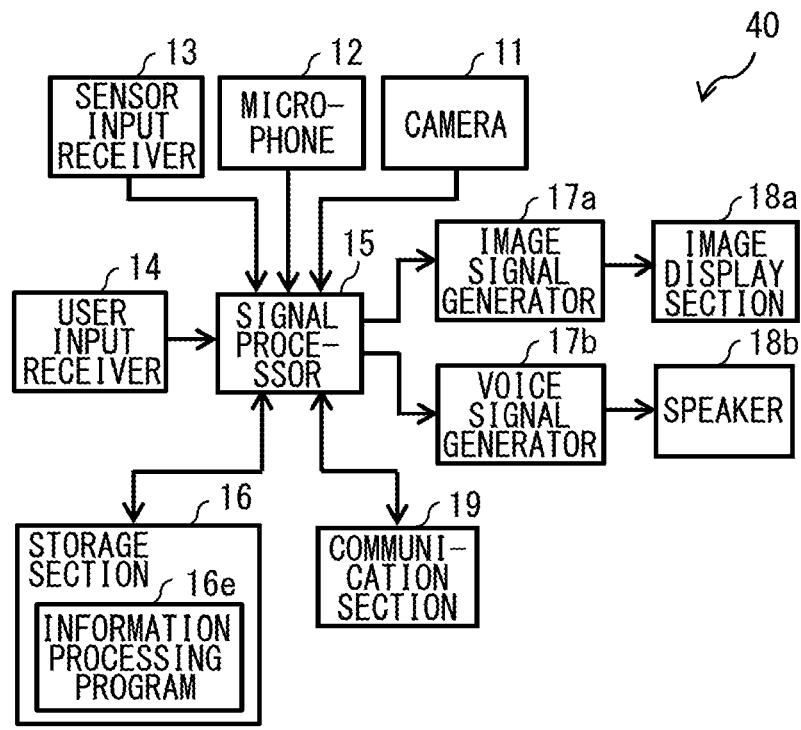
[ FIG. 7 ]
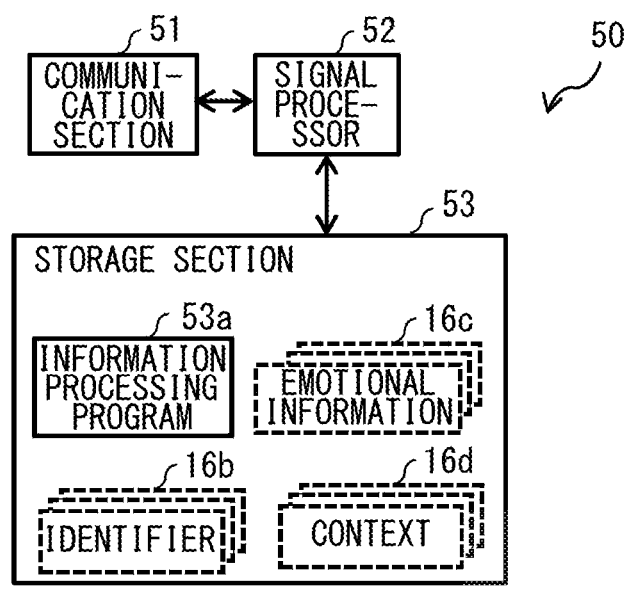

[ FIG. 8 ]
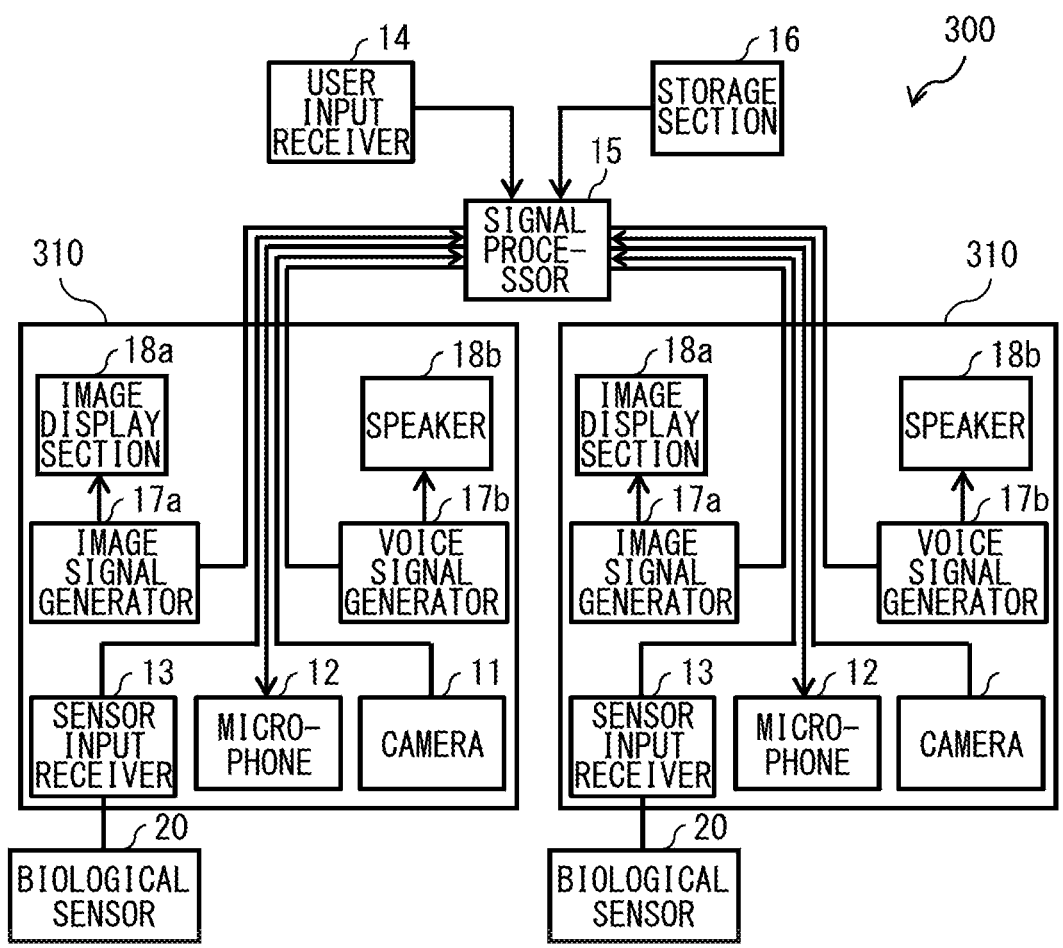

[ FIG. 9 ]
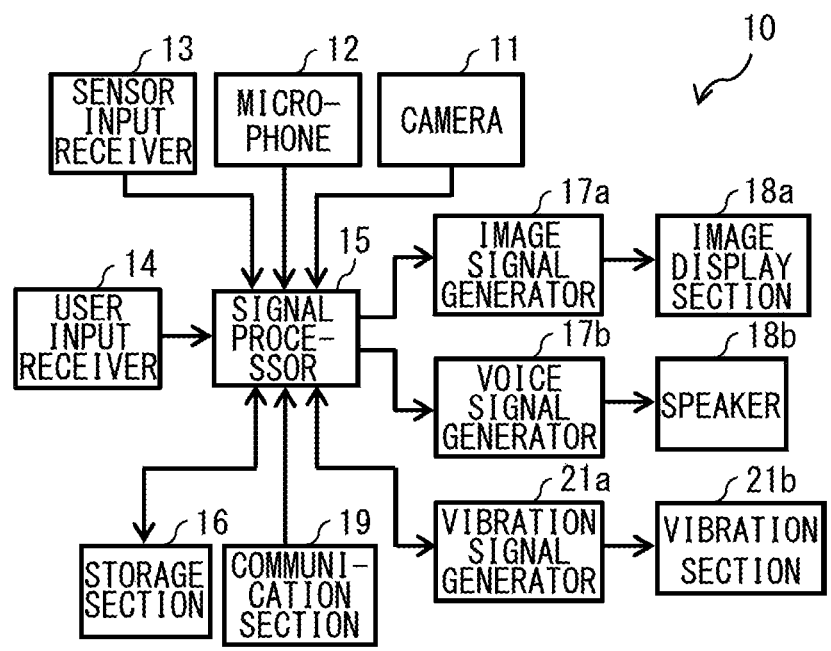
[ FIG. 10 ]
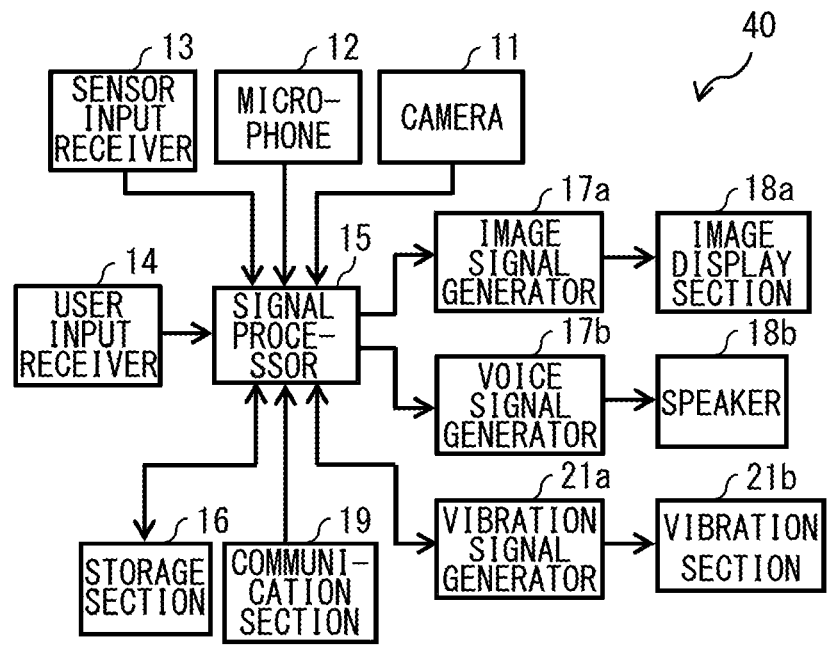

[ FIG. 11 ]
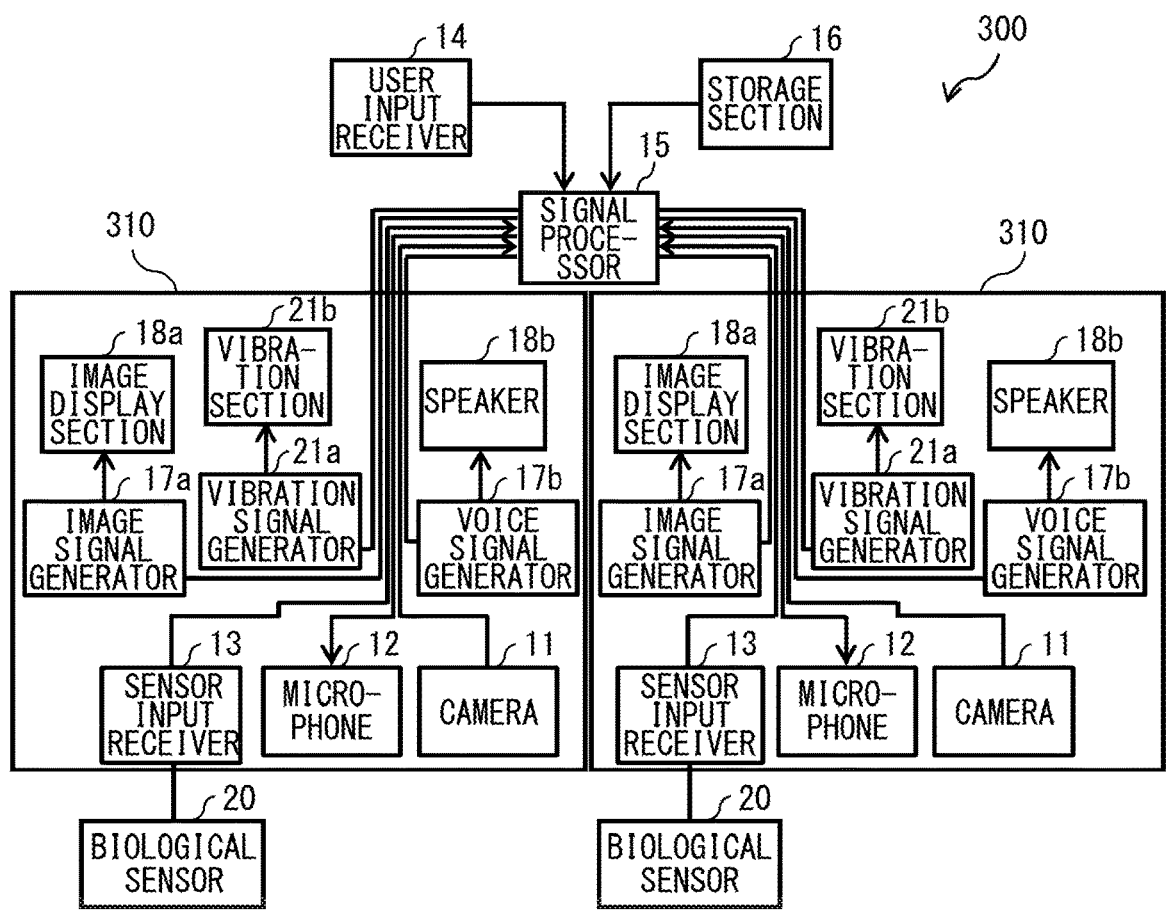

[ FIG. 12 ]
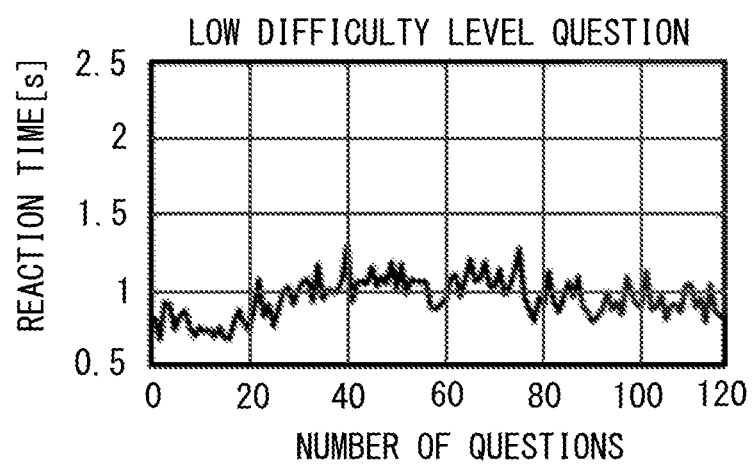
[ FIG. 13 ]
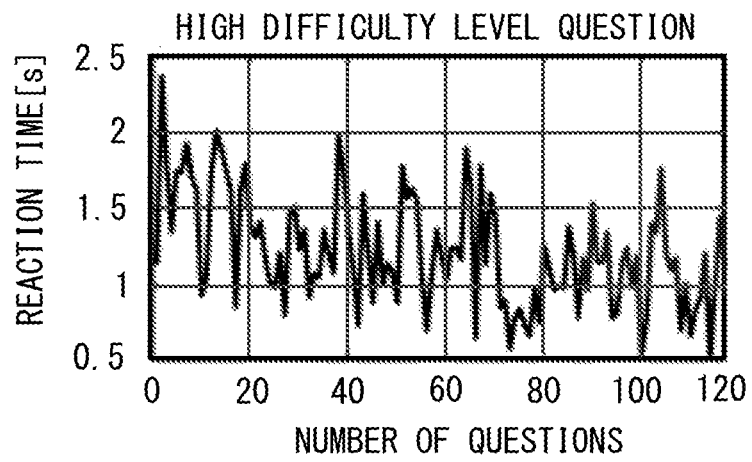

[ FIG. 14 ]
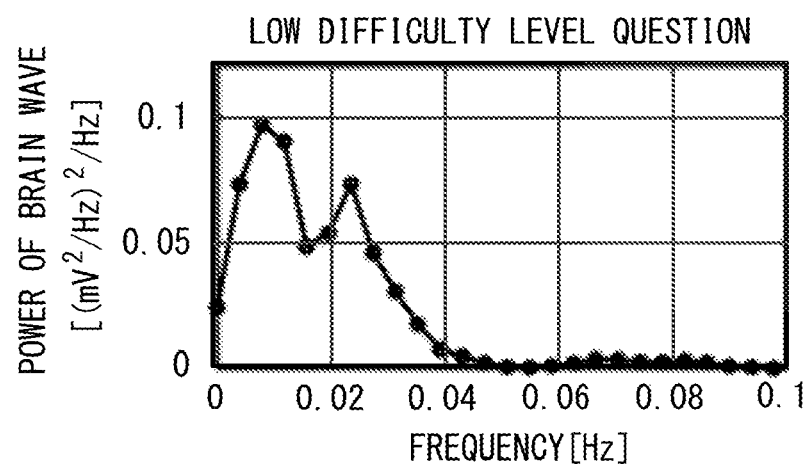
[ FIG. 15 ]
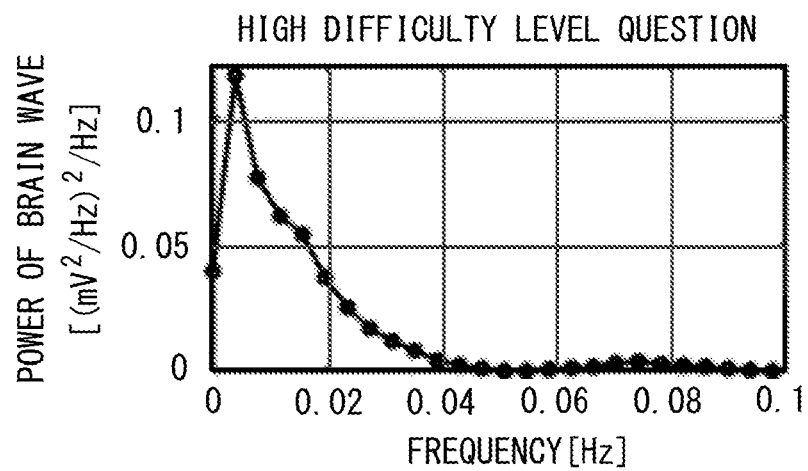

[ FIG. 16 ]
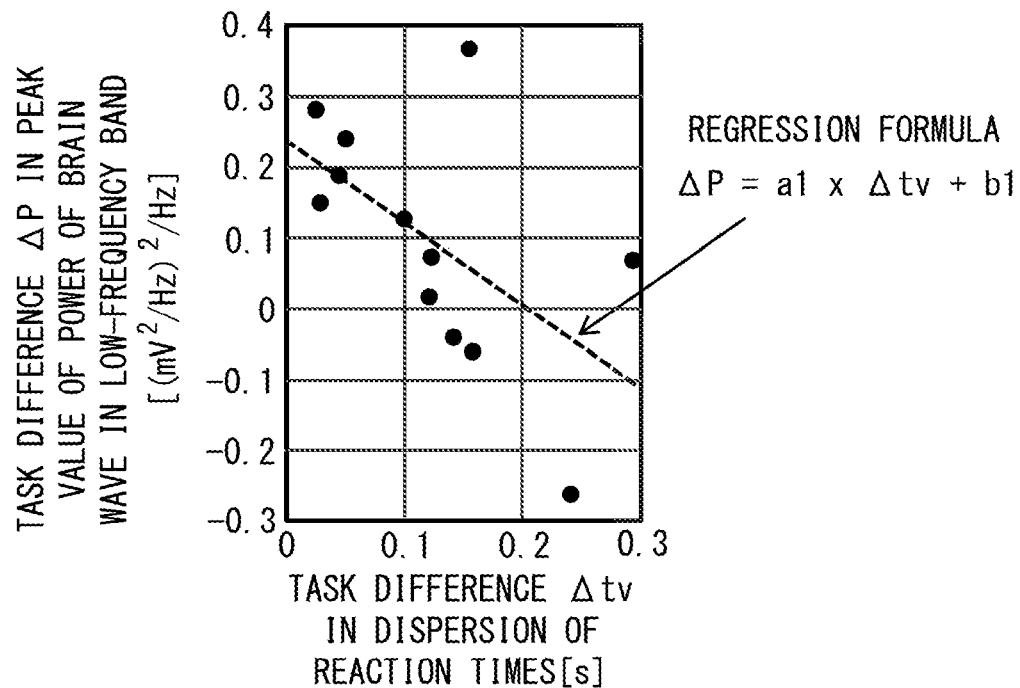
[ FIG. 17 ]
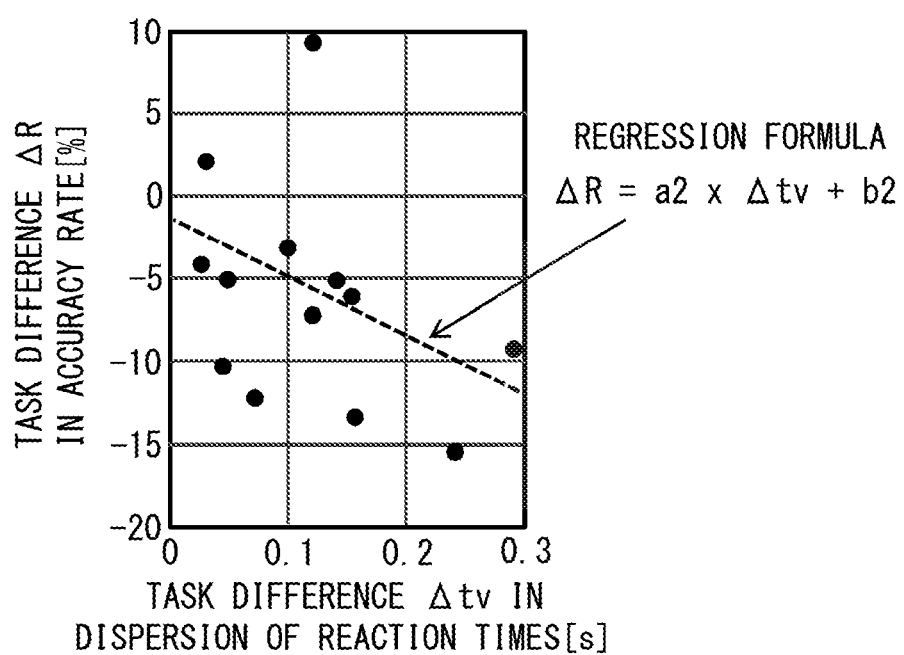

[ FIG. 18 ]
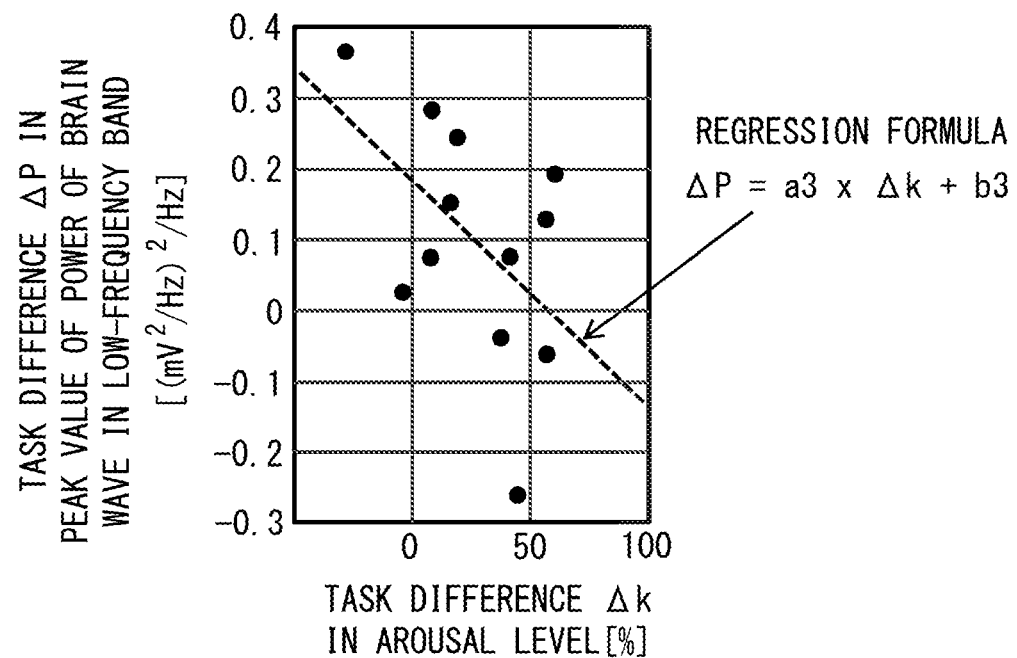
[ FIG. 19 ]
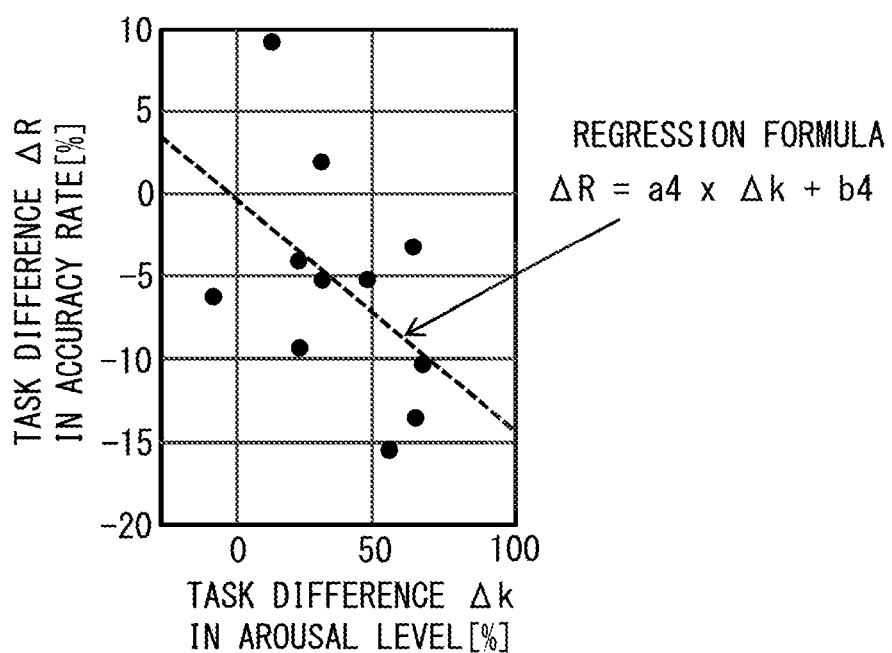

[ FIG. 20 ]
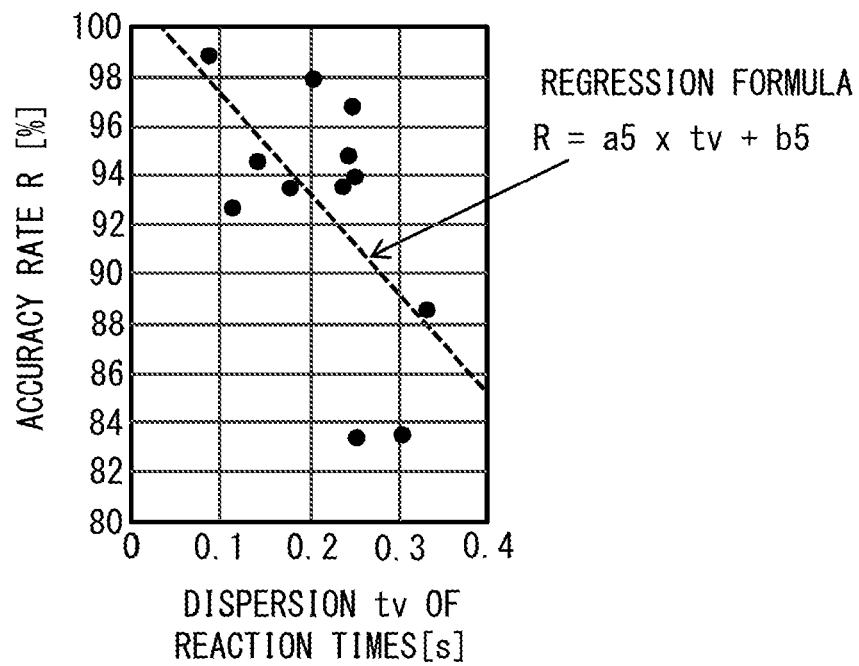
[ FIG. 21 ]
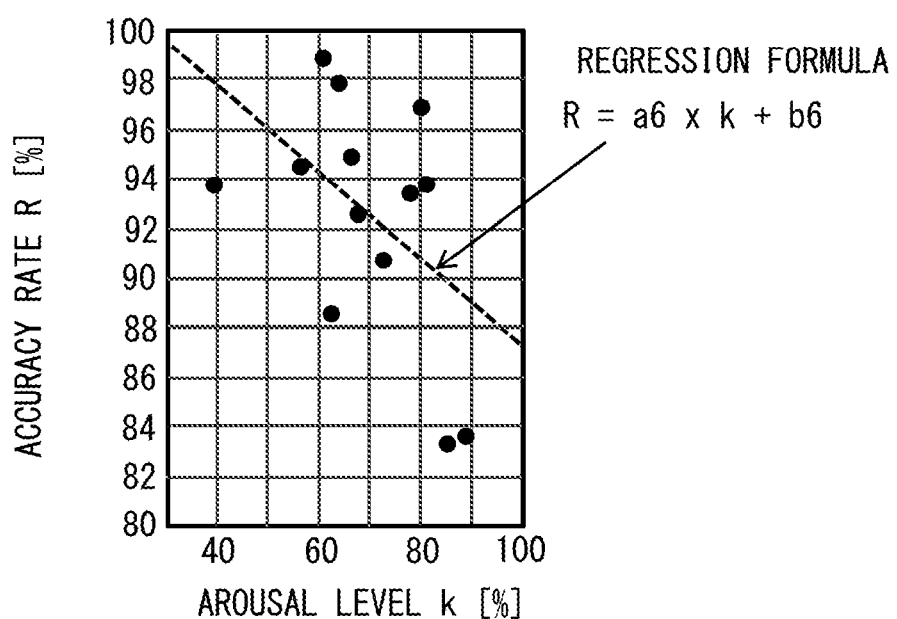

[ FIG. 22 ]
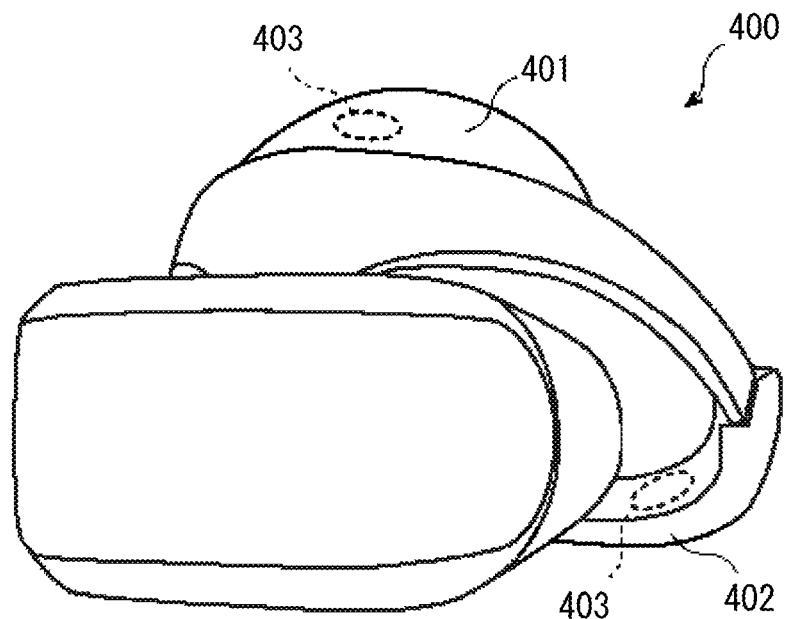
[ FIG. 23 ]
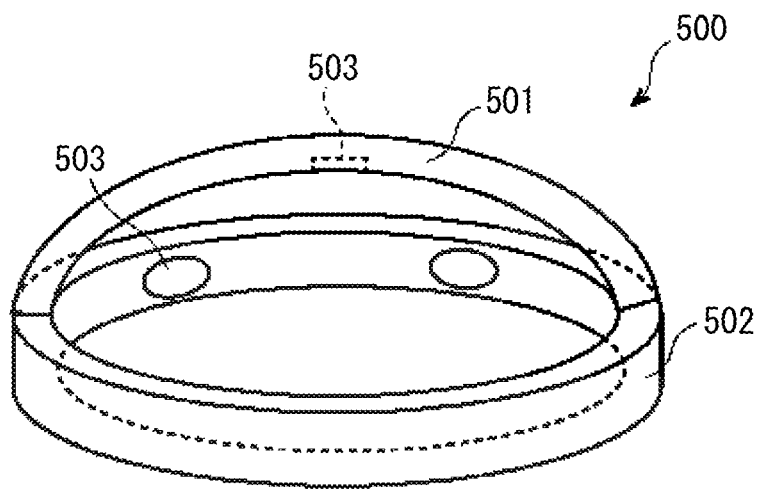

[ FIG. 24 ]
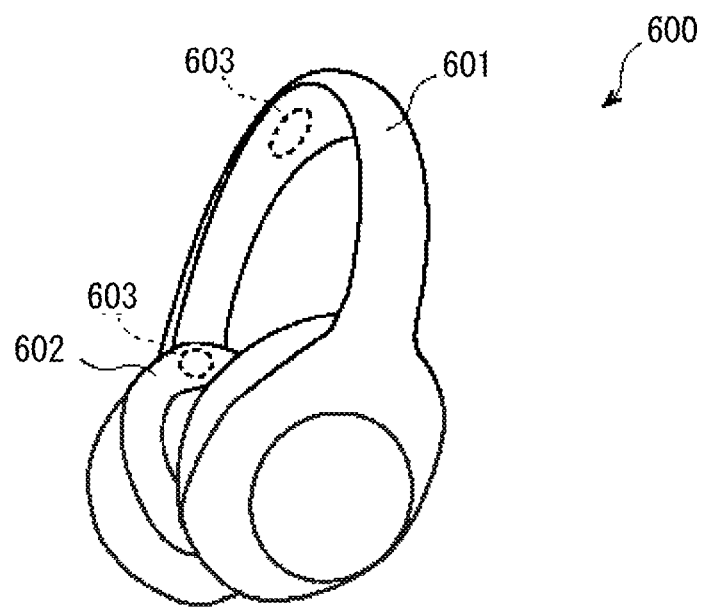
[ FIG. 25 ]
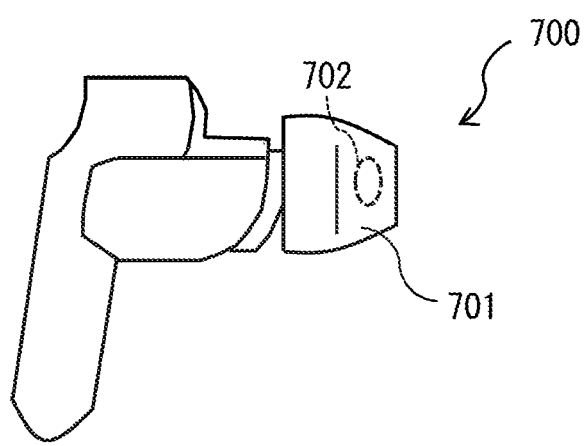

[ FIG. 26 ]
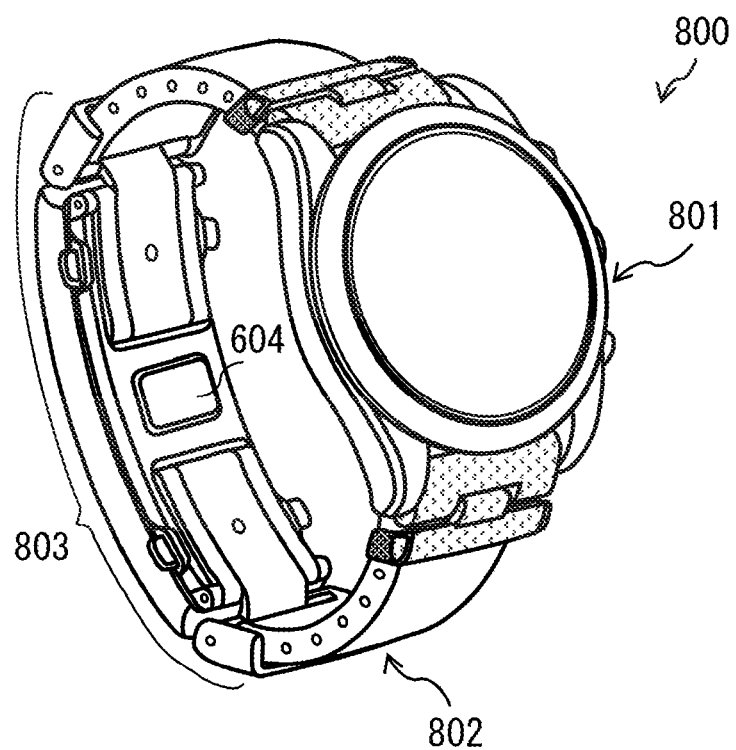
[ FIG. 27 ]
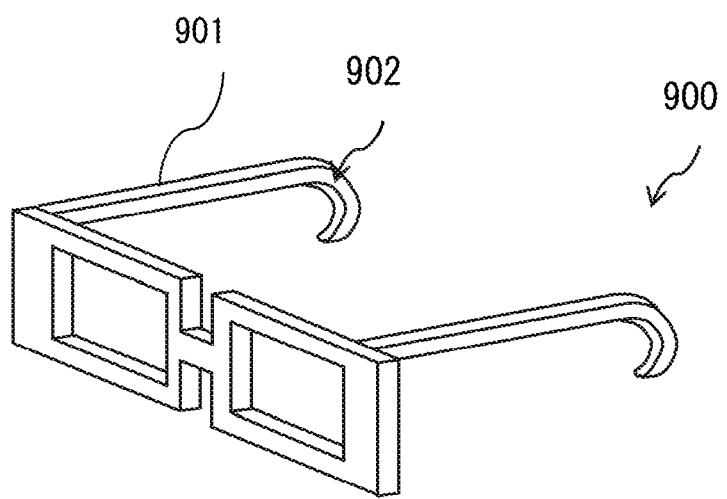

[ FIG. 28 ]
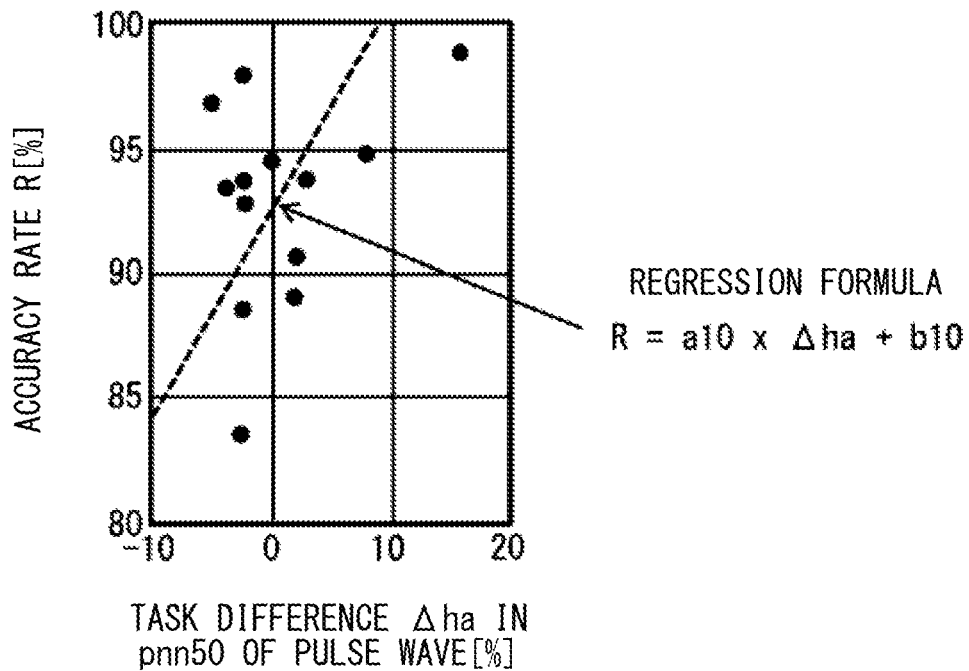
[ FIG. 29 ]
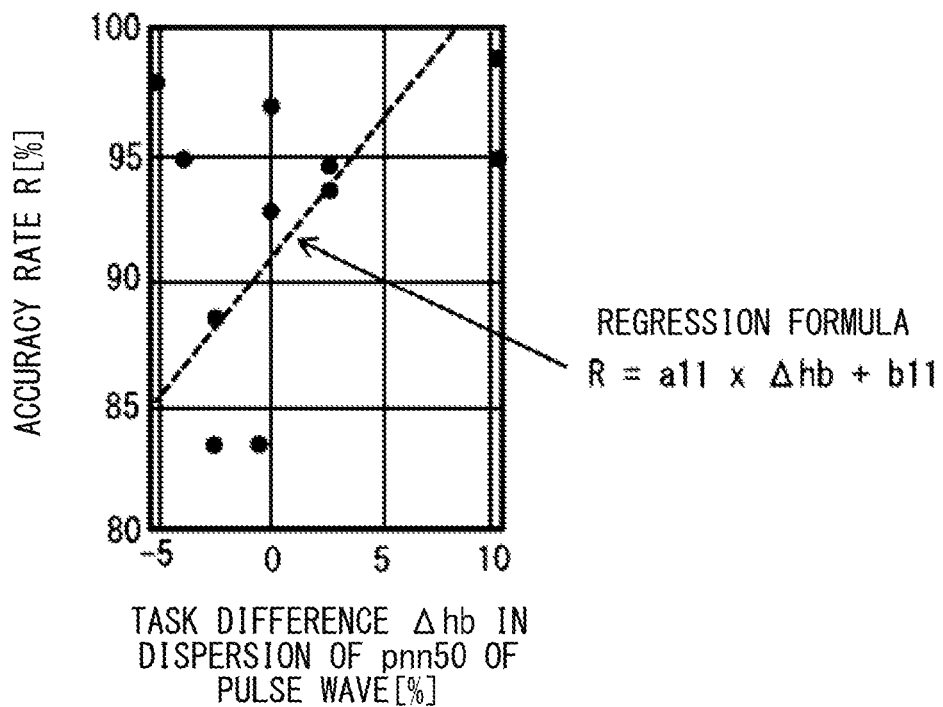

[ FIG. 30 ]
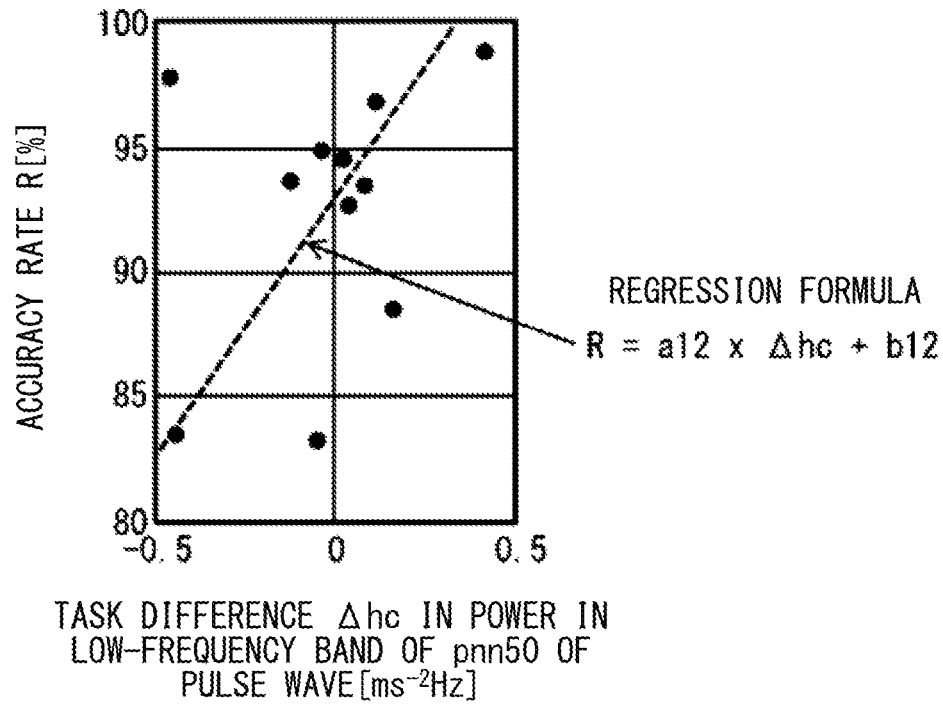
[ FIG. 31 ]
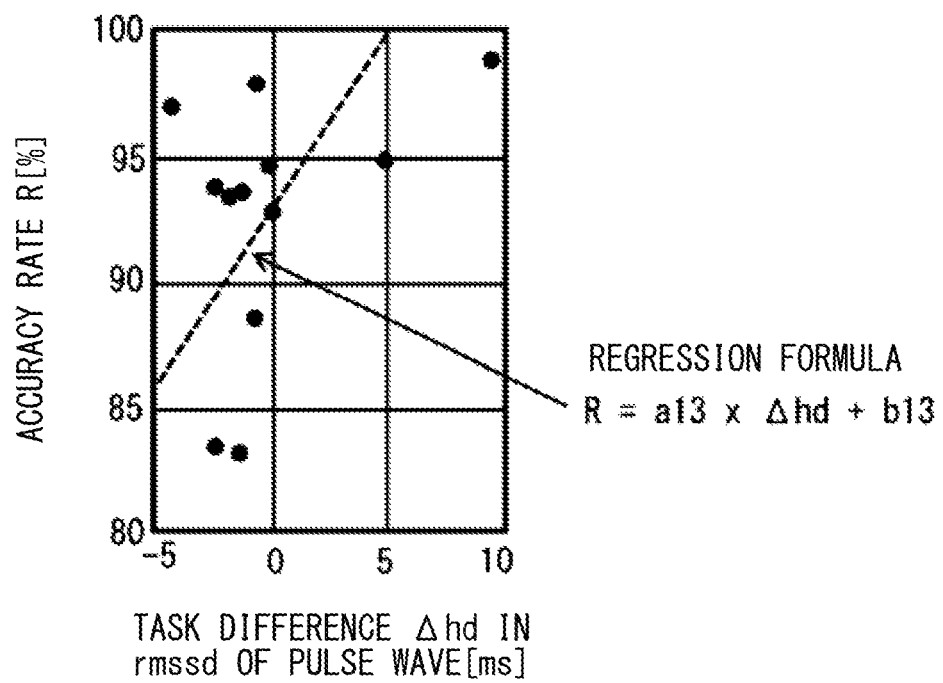

[ FIG. 32 ]
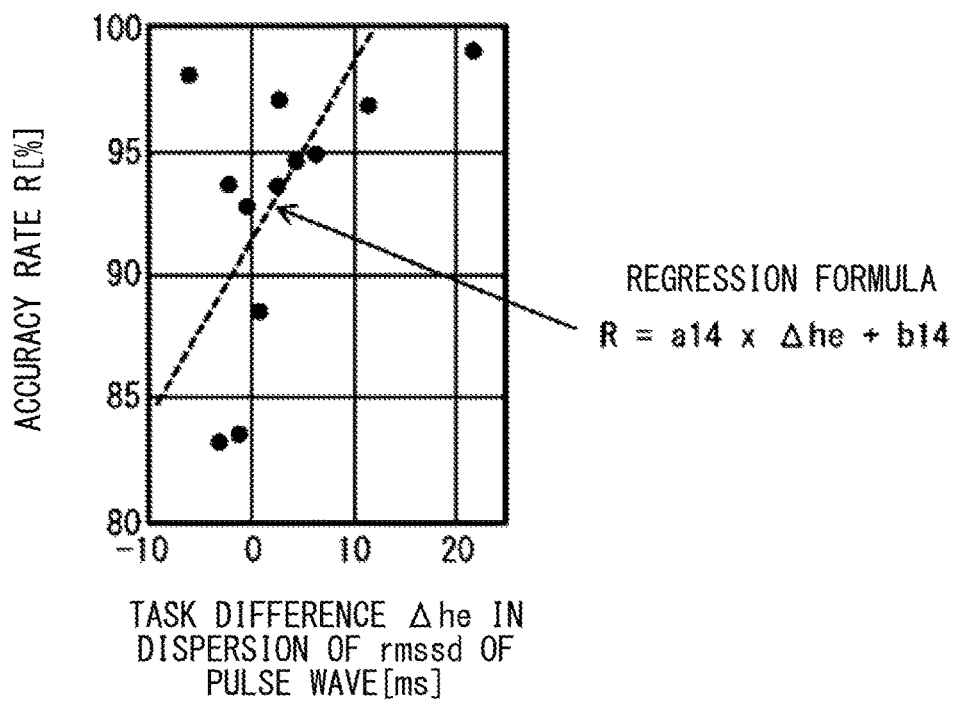
[ FIG. 33 ]
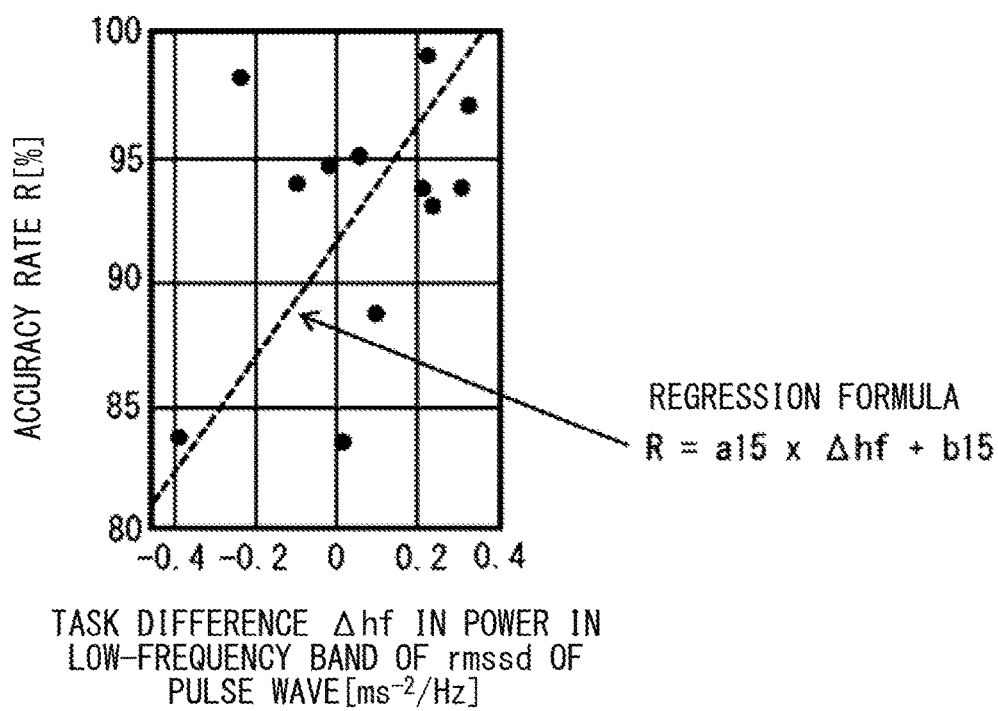

[ FIG. 34 ]
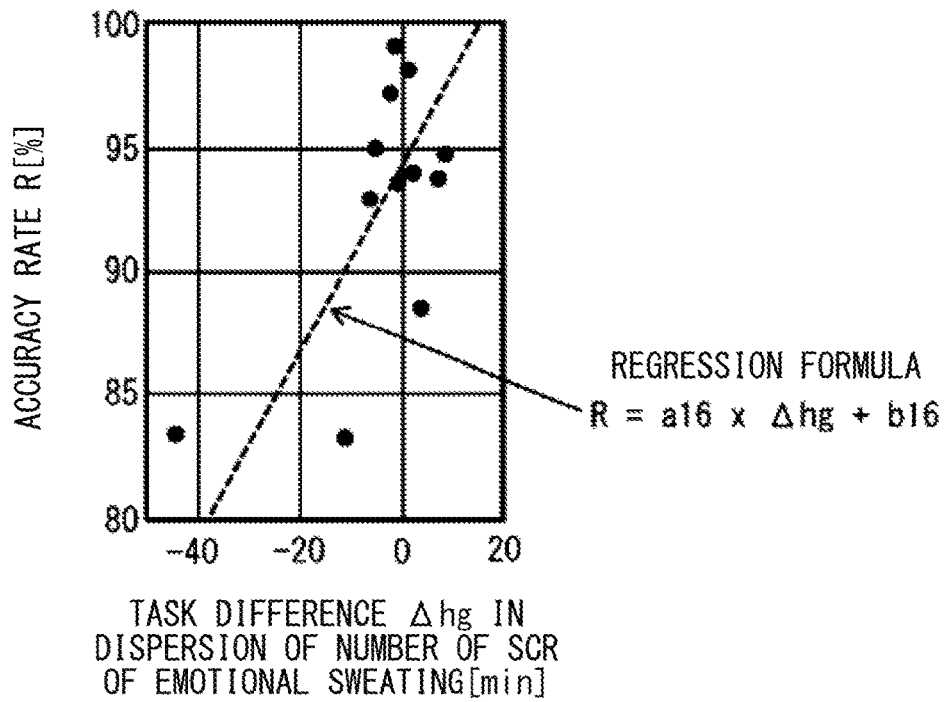
[ FIG. 35 ]
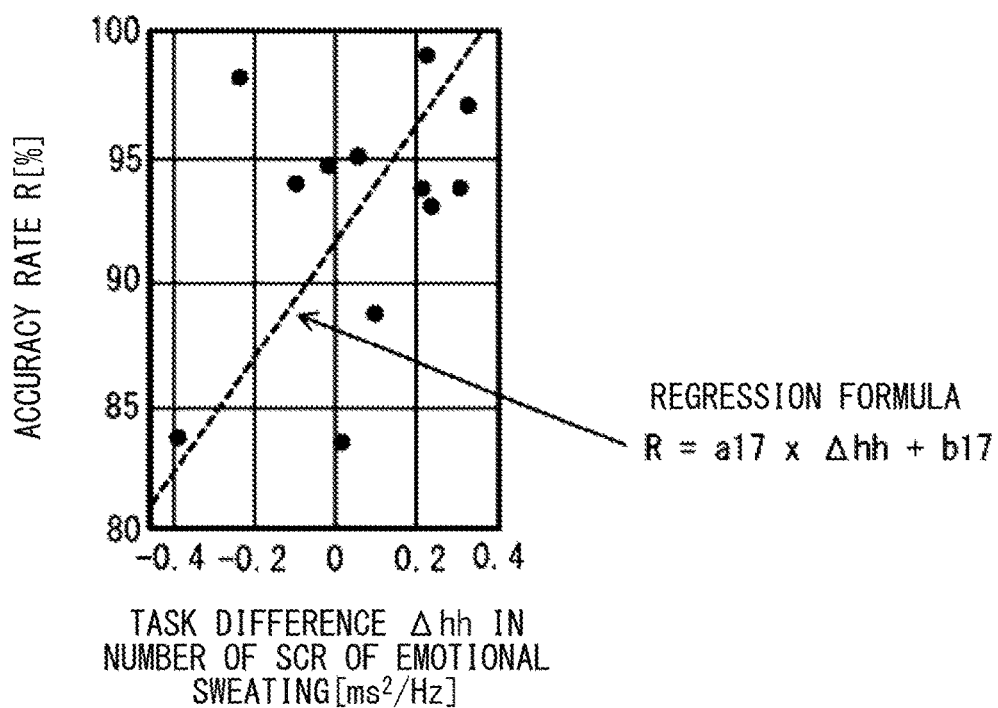

[ FIG. 36 ]
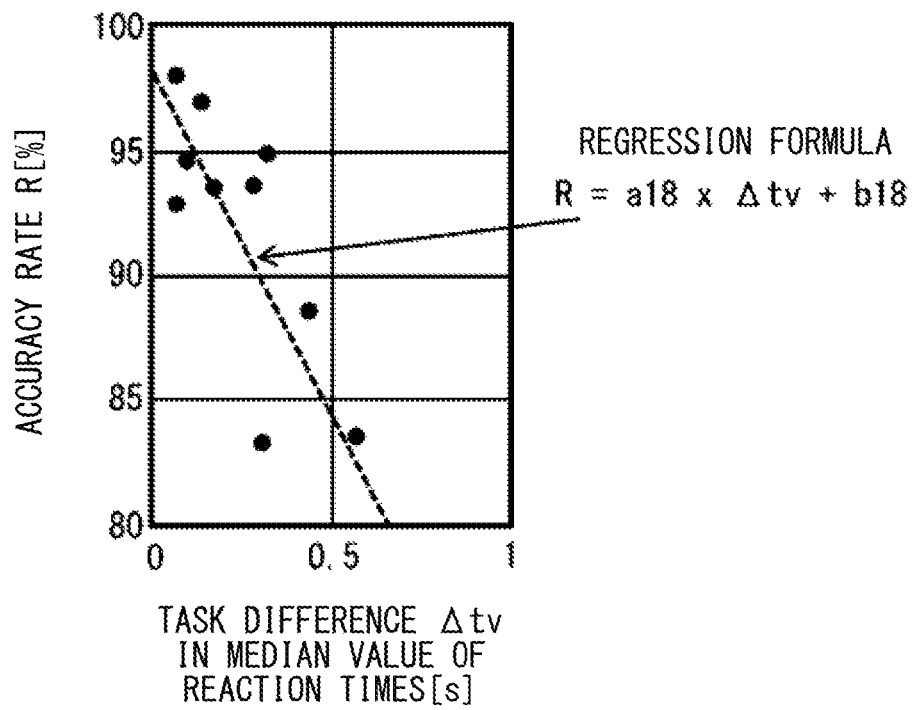
[ FIG. 37 ]
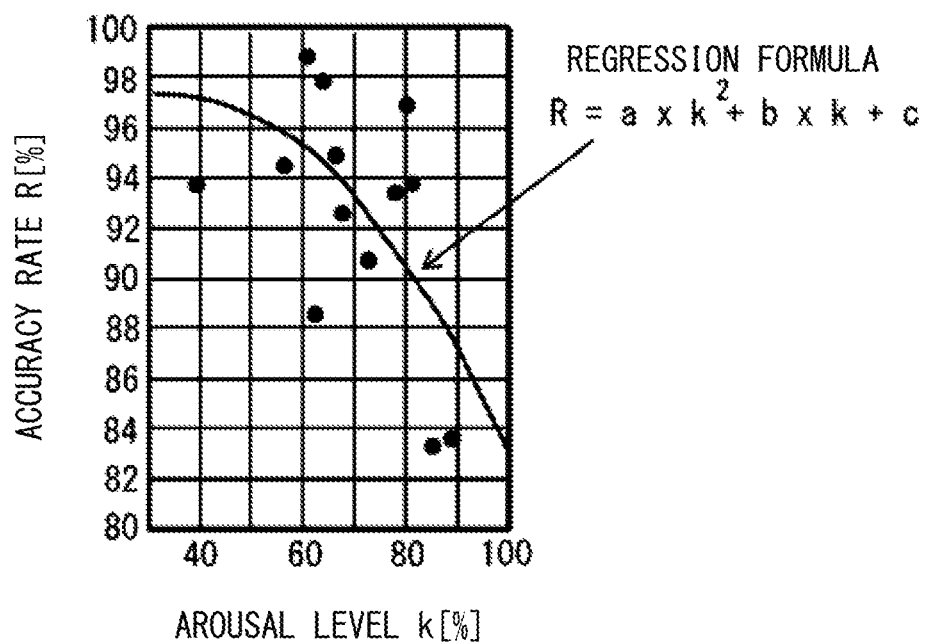

INFORMATION PROCESSING SYSTEM DISPLAYING EMOTIONAL INFORMATION

CROSS REFERENCE TO RELATED APPLICATIONS

This application is a U.S. National Phase of International Patent Application No. PCT/JP2022/008063 filed on Feb. 25, 2022, which claims priority benefits of Japanese Patent Application No. JP 2021-056032 filed in the Japan Patent Office on Mar. 29, 2021 and Japanese Patent Application No. JP 2021-132938 filed in the Japan Patent Office on Aug. 17, 2021. Each of the above-referenced applications is hereby incorporated herein by reference in its entirety.

TECHNICAL FIELD

The present disclosure relates to an information processing system.

BACKGROUND ART

In a case where a plurality of persons builds an interpersonal relationship, personalities of other persons and an element necessary for relationship building with the other persons are inferred from mutually observable information. However, such an inference is uncertain, which generally makes it difficult to build an interpersonal relationship with a congenial person. In addition, uncertainty of the inference causes an opportunity loss of building the interpersonal relationship.

For example, PTL 1 describes that mutual congeniality is determined on the basis of the action history of a person, and preference information and attribute information about the person.

CITATION LIST

Patent Literature

PTL 1: Japanese Unexamined Patent Application Publication No. 2020-35344

SUMMARY OF THE INVENTION

However, it is difficult to say that the action history of a person, and preference information and attribute information about the person are information suitable for accurately determining mutual congeniality. It is therefore desirable to provide an information processing system that makes it possible to more accurately determine mutual congeniality.

An information processing system according to a first aspect of the present disclosure includes an estimation section and a display section. The estimation section estimates emotional information about a target living body on the basis of at least one of biological information or motion information about the target living body acquired by a sensor. The display section displays the emotional information on a display surface.

An information processing system according to a second aspect of the present disclosure includes a first estimation section, a second estimation section, and a display section. The first estimation section estimates emotional information about a first target living body on the basis of at least one of first biological information or first motion information about the first target living body acquired by a first sensor. The second estimation section estimates emotional information about a second target living body on the basis of at least one of second biological information or second motion information about the second target living body acquired by a second sensor. The display section displays the emotional information acquired by the first estimation section and the emotional information acquired by the second estimation section together on a display surface.

An information processing system according to a third aspect of the present disclosure includes an estimation section, an acquisition section, and an association section. The estimation section estimates emotional information about a target living body on the basis of at least one of biological information or motion information about the target living body acquired by a sensor. The acquisition section acquires a context in a sensing period by the sensor. The association section associates the emotional information acquired by the estimation section and the context acquired by the acquisition section with each other.

An information processing system according to a fourth aspect of the present disclosure includes a first estimation section, a second estimation section, an acquisition section, and an association section. The first estimation section estimates emotional information about a first target living body on the basis of at least one of first biological information or first motion information about the first target living body acquired by a first sensor. The second estimation section estimates emotional information about a second target living body on the basis of at least one of second biological information or second motion information about the second target living body acquired by a second sensor. The acquisition section acquires a context in a sensing period by the first sensor and the second sensor. The association section associates the emotional information acquired by the first estimation section, the emotional information acquired by the second estimation section, and the context acquired by the acquisition section in association with each other.

In the information processing system according to the first aspect of the present disclosure, the emotional information about the target living body is estimated on the basis of at least one of the biological information or the motion information about the target living body acquired by the sensor, and is displayed on the display surface. Accordingly, for example, in a case where the target living body is a communication partner, a user is able to infer an element necessary for relationship building with the partner on the basis of the emotional information about the partner. Herein, the emotional information about the partner is objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. In addition, for example, in a case where the target living body is the user oneself, the user is able to infer the element necessary for relationship building with the partner on the basis of the emotional information about the user oneself. Herein, the emotional information about the user oneself is objective information acquired in a process of mutual communication. Accordingly, it is possible to perform more accurate inference, as compared with a case of inferring the element necessary for relationship building with the partner on the basis of the action history of the partner, and preference information and attribute information about the partner.

In the information processing system according to the second aspect of the present disclosure, the emotional information about the first target living body is estimated on the basis of at least one of the first biological information or the first motion information about the first target living body acquired by the first sensor. Furthermore, the emotional information about the second target living body is estimated on the basis of at least one of the second biological information or the second motion information about the second target living body acquired by the second sensor. Then, the emotional information acquired by the first estimation section and the emotional information acquired by the second estimation section are displayed together on the display surface. Accordingly, in a case where the first target living body is a user oneself and the second target living body is a communication partner, the user is able to infer the element necessary for relationship building with the partner on the basis of both the emotional information acquired by the first estimation section and the emotional information acquired by the second estimation section. Herein, both the emotional information acquired by the first estimation section and the emotional information acquired by the second estimation section are objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner.

In the information processing system according to the third aspect of the present disclosure, the emotional information about the target living body is estimated on the basis of at least one of the biological information or the motion information about the target living body acquired by the sensor. Furthermore, the context in the sensing period by the sensor is acquired. Then, the emotional information acquired by the estimation section and the context acquired by the acquisition section are associated with each other. Accordingly, for example, in a case where the target living body is a communication partner, a user is able to infer the element necessary for relationship building with the partner on the basis of emotional information about the partner. Herein, the emotional information about the partner is objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. In addition, for example, in a case where the target living body is the user oneself, the user is able to infer the element necessary for relationship building with the partner on the basis of the emotional information about the user oneself Herein, the emotional information about the user oneself is objective information acquired in a process of mutual communication. Accordingly, it is possible to perform more accurate inference, as compared with a case of inferring the element necessary for relationship building with the partner on the basis of the action history of the partner, and preference information and attribute information about the partner.

In the information processing system according to the fourth aspect of the present disclosure, the emotional information about the first target living body is estimated on the basis of at least one of the first biological information or the first motion information about the first target living body acquired by the first sensor. Furthermore, the emotional information about the second target living body is estimated on the basis of at least one of the second biological information or the second motion information about the second target living body acquired by the second sensor. Furthermore, the context in the sensing period by the first sensor and the second sensor is acquired. Then, the emotional information acquired by the first estimation section, the emotional information acquired by the second estimation section, and the context acquired by the acquisition section are associated with each other. Accordingly, for example, in a case where the first target living body is a user oneself and the second target living body is a communication partner, the user is able to infer the element necessary for relationship building with the partner on the basis of both the emotional information acquired by the first estimation section and the emotional information acquired by the second estimation section. Herein, both the emotional information acquired by the first estimation section and the emotional information acquired by the second estimation section are objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner.

BRIEF DESCRIPTION OF DRAWINGS

FIG. 1 is a diagram illustrating an example of a schematic configuration of an information processing system according to a first embodiment of the present disclosure.

FIG. 2 is a diagram illustrating an example of functional blocks of an electronic apparatus in FIG. 1.

FIG. 3 is a diagram illustrating an example of screen display of the electronic apparatus in FIG. 1.

FIG. 4 is a diagram illustrating an example of the screen display of the electronic apparatus in FIG. 1.

FIG. 5 is a diagram illustrating an example of a schematic configuration of an information processing system according to a second embodiment of the present disclosure.

FIG. 6 is a diagram illustrating an example of functional blocks of an electronic apparatus in FIG. 5.

FIG. 7 is a diagram illustrating an example of functional blocks of a server apparatus in FIG. 5.

FIG. 8 is a diagram illustrating an example of a schematic configuration of an information processing device according to a third embodiment of the present disclosure.

FIG. 9 is a diagram illustrating a modification example of the functional blocks of the electronic apparatus in FIG. 2.

FIG. 10 is a diagram illustrating a modification example of the functional blocks of the electronic apparatus in FIG. 6.

FIG. 11 is a diagram illustrating a modification example of the schematic configuration of the information processing device in FIG. 8.

FIG. 12 is a diagram illustrating an example of time series data of reaction times for low difficulty level questions.

FIG. 13 is a diagram illustrating an example of time series data of reaction times for high difficulty level questions.

FIG. 14 is a diagram illustrating an example of a power spectrum density obtained by performing FFT (Fast Fourier Transform) on observation data of a brain wave (α-wave) of a user when solving low difficulty level questions.

FIG. 15 is a diagram illustrating an example of a power spectrum density obtained by performing FFT (Fast Fourier Transform) on observation data of a brain wave (α-wave) of the user when solving high difficulty level questions.

FIG. 16 is a diagram illustrating an example of a relationship between a task difference in dispersion of reaction times and a task difference in a peak value of power of a brain wave in a low-frequency band.

FIG. 17 is a diagram illustrating an example of a relationship between a task difference in dispersion of reaction times and a task difference in an accuracy rate.

FIG. 18 is a diagram illustrating an example of a relationship between a task difference in an arousal level and a task difference in the peak value of the power of the brain wave in the low-frequency band.

FIG. 19 is a diagram illustrating an example of a relationship between the task difference in the arousal level and the task difference in the accuracy rate.

FIG. 20 is a diagram illustrating an example of a relationship between the dispersion of the reaction times and the accuracy rate.

FIG. 21 is a diagram illustrating an example of a relationship between the arousal level and the accuracy rate.

FIG. 22 is a diagram illustrating an example of a head-mounted display mounted with a sensor.

FIG. 23 is a diagram illustrating an example of a head band mounted with a sensor.

FIG. 24 is a diagram illustrating an example of a headphone mounted with a sensor.

FIG. 25 is a diagram illustrating an example of an earphone mounted with a sensor.

FIG. 26 is a diagram illustrating an example of a watch mounted with a sensor.

FIG. 27 is a diagram illustrating an example of glasses mounted with a sensor.

FIG. 28 is a diagram illustrating an example of a relationship between a task difference in pnn50 of a pulse wave and the accuracy rate.

FIG. 29 is a diagram illustrating an example of a relationship between a task difference in dispersion of the pnn50 of the pulse wave and the accuracy rate.

FIG. 30 is a diagram illustrating an example of a relationship between a task difference in power of the pnn50 of the pulse wave in the low-frequency band and the accuracy rate.

FIG. 31 is a diagram illustrating an example of a relationship between a task difference in rmssd of the pulse wave and the accuracy rate.

FIG. 32 is a diagram illustrating an example of a task difference in dispersion of the rmssd of the pulse wave and the accuracy rate.

FIG. 33 is a diagram illustrating an example of a relationship between a task difference in power of the rmssd of the pulse wave in the low-frequency band and the accuracy rate.

FIG. 34 is a diagram illustrating an example of a relationship between a task difference in dispersion of the number of SCRs of emotional sweating and the accuracy rate.

FIG. 35 is a diagram illustrating an example of a relationship between a task difference in the number of SCRs of the emotional sweating and the accuracy rate.

FIG. 36 is a diagram illustrating an example of a relationship between a task difference in a median value of reaction times and the accuracy rate.

FIG. 37 is a diagram illustrating an example of a relationship between the arousal level and the accuracy rate.

MODES FOR CARRYING OUT THE INVENTION

In the following, some embodiments of the present disclosure are described in detail with reference to the drawings.

1. About Arousal Level

The arousal level of a person is closely related to concentration of the person. A person in concentration is highly interested and concerned in an object on which the person is concentrated. Accordingly, it is possible to estimate an objective interest/concern degree (emotion) of the person by knowing the arousal level of the person. It is possible to derive the arousal level of the person on the basis of biological information or motion information acquired from oneself who is in conversation with a communication partner or the communication partner (hereinafter referred to as a "target living body").

Examples of the biological information from which an arousal level of the target living body is derivable include information about a brain wave, sweating, a pulse wave, an electrocardiogram, a blood flow, a skin temperature, potential of facial muscles, eye potential, a specific component contained in saliva.

(Brain Wave)

It is known that α-waves included in brain waves increase when a person is relaxed such as when resting, and β-waves included in brain waves increase when the person is doing actively active thinking or is in concentration. Accordingly, for example, when a power spectrum area in a frequency band of the α-wave included in the brain wave is smaller than a predetermined threshold 1 and a power spectrum area in a frequency band of the 3-wave included in the brain wave is larger than a predetermined threshold th2, it is possible to estimate that the arousal level of the target living body is high.

In addition, in estimating the arousal level of the target living body with use of the brain wave, it is possible to use an estimation model such as machine learning in place of the thresholds th1 and th2. This estimation model is, for example, a model trained using, as teaching data, a power spectrum of the brain wave when the arousal level is apparently high. For example, in a case where a power spectrum of the brain wave is inputted, this estimation model estimates the arousal level of the target living body on the basis of the inputted power spectrum of the brain wave. This estimation model includes, for example, a neural network. This learning model may include, for example, a deep neural network such as a convolutional neural network (CNN).

In addition, the brain wave may be divided into a plurality of segments on a time axis, and a power spectrum may be derived for each of divided segments to derive a power spectrum area in the frequency band of the α-wave for each derived power spectrum. In this case, for example, when the derived power spectrum area is smaller than a predetermined threshold tha, it is possible to estimate that the arousal level of the target living body is high.

In addition, it is possible to estimate the arousal level of the target living body with use of, for example, an estimation model that estimates the arousal level of the target living body on the basis of the derived power spectrum area. This estimation model is, for example, a model trained using, as teaching data, a power spectrum area when the arousal level is apparently high. For example, in a case where a power spectrum area is inputted, this estimation model estimates the arousal level of the target living body on the basis of the inputted power spectrum area. This estimation model includes, for example, a neural network. This learning model may include, for example, a deep neural network such as a convolutional neural network (CNN).

(Sweating)

Emotional sweating is sweating released from eccrine sweat glands when sympathetic nerves are strained due to a mental/psychological issue such as stress, tension, or anxiety. For example, a sweat sensor probe is attached to a palm or a sole, and sweating (emotional sweating) on the palm or the sole induced by various load stimuli is measured, which makes it possible to obtain a sympathetic sweat response (SSwR) as a signal voltage. When a numeric value of a predetermined high-frequency component or a predetermined low-frequency component in this signal voltage is higher than a predetermined threshold, it is possible to estimate that the arousal level of the target living body is high.

In addition, it is possible to estimate the arousal level of the target living body with use of, for example, an estimation model that estimates the arousal level of the target living body on the basis of the predetermined high-frequency component or the predetermined low-frequency component included in this signal voltage. This estimation model is, for example, a model trained using, as teaching data, a predetermined high-frequency component or a predetermined low-frequency component included in a signal voltage when the arousal level is apparently high. For example, in a case where the predetermined high-frequency component or the predetermined low-frequency component is inputted, this estimation model estimates the arousal level of the target living body on the basis of the inputted predetermined high-frequency component or the inputted predetermined low-frequency component. This estimation model includes, for example, a neural network. This learning model may include, for example, a deep neural network such as a convolutional neural network (CNN).

(Pulse Wave, Electrocardiogram, and Blood Flow)

It is generally said that, when a heart rate is high, the arousal level is high. It is possible to derive the heart rate from a pulse wave, an electrocardiogram, or blood flow velocity. Accordingly, for example, when the heart rate is derived from the pulse wave, the electrocardiogram, or the blood flow velocity and the derived heart rate is larger than a predetermined threshold, it is possible to estimate that the arousal level of the target living body is high.

In addition, it is possible to estimate the arousal level of the target living body with use of, for example, an estimation model that estimates the arousal level of the target living body on the basis of the heart rate derived from the pulse wave, the electrocardiogram, or the blood flow velocity. This estimation model is, for example, a model trained using, as teaching data, a heart rate when the arousal level is apparently high. In a case where a heart rate derived from the pulse wave, the electrocardiogram, or the blood flow velocity is inputted, this estimation model estimates the arousal level of the target living body on the basis of the inputted heart rate. This estimation model includes, for example, a neural network. This learning model may include, for example, a deep neural network such as a convolutional neural network (CNN).

In addition, it is generally said that, when heart rate variability (HRV) is small, parasympathetic nerves become subordinate and the arousal level is high. Accordingly, for example, when the heart rate variability (HRV) is derived from the pulse wave, the electrocardiogram, or the blood flow velocity and the derived heart rate variability (HRV) is smaller than a predetermined threshold, it is possible to estimate that the arousal level of the target living body is high.

In addition, it is possible to estimate the arousal level of the target living body with use of, for example, an estimation model that estimates the arousal level of the target living body on the basis of the heart rate variability (HRV) derived from the pulse wave, the electrocardiogram, or the blood flow velocity. This estimation model is, for example, a model trained using, as teaching data, heart rate variability (HRV) when the arousal level is apparently high. For example, in a case where heart rate variability (HRV) derived from the pulse wave, the electrocardiogram, or the blood flow velocity is inputted, this estimation model estimates the arousal level of the target living body on the basis of the inputted heart rate variability (HRV). This estimation model includes, for example, a neural network. This learning model may include, for example, a deep neural network such as a convolutional neural network (CNN).

(Skin Temperature)

It is generally said that, when a skin temperature is high, the arousal level is high. It is possible to measure the skin temperature by, for example, thermography. Accordingly, for example, when the skin temperature measured by the thermography is higher than a predetermined threshold, it is possible to estimate that the arousal level of the target living body is high.

In addition, it is possible to estimate the arousal level of the target living body with of, for example, an estimation model that estimates the arousal level of the target living body on the basis of the skin temperature. This estimation model is, for example, a model trained using, as teaching data, a skin temperature when the arousal level is apparently high. For example, in a case where a skin temperature is inputted, this estimation model estimates the arousal level of the target living body on the basis of the inputted skin temperature. This estimation model includes, for example, a neural network. This learning model may include, for example, a deep neural network such as a convolutional neural network (CNN).

(Potential of Facial Muscles)

It is known that corrugator supercilii muscles involved in frowning show high activity when thinking about something. In addition, it is known that zygomaticus major muscles hardly change when thinking about happy things. Thus, it is possible to estimate emotion or the arousal level in accordance with facial parts. Accordingly, for example, when potential of facial muscles in a predetermined part is measured and a thus-obtained measurement value is higher than a predetermined threshold, it is possible to estimate whether the arousal level of the target living body is high or low.

In addition, it is possible to estimate the arousal level of the target living body with use of, for example, an estimation model that estimates the arousal level of the target living body on the basis of the potential of facial muscles. This estimation model is, for example, a model trained using, as teaching data, potential of facial muscles when the arousal level is apparently high. For example, in a case where potential of facial muscles is inputted, this estimation model estimates the arousal level of the target living body on the basis of the inputted potential of facial muscles. This estimation model includes, for example, a neural network. This learning model may include, for example, a deep neural network such as a convolutional neural network (CNN).

(Eye Potential)

A method is known of measuring eyeball movement with use of a positively charged cornea and a negatively charged retina in a eyeball. A measurement value obtained by using this measuring method is an electrooculogram. For example, in a case where the eyeball movement is estimated from an obtained electrooculogram and the estimated eyeball movement has a predetermined tendency, it is possible to estimate whether the arousal level of the target living body is high or low.

In addition, it is possible to estimate the arousal level of the target living body with use of, for example, an estimation model that estimates the arousal level of the target living body on the basis of the electrooculogram. This estimation model is, for example, a model trained using, as teaching data, an electrooculogram when the arousal level is apparently high. For example, in a case where an electrooculogram is inputted, this estimation model estimates the arousal level of the target living body on the basis of the inputted electrooculogram. This estimation model includes, for example, a neural network. This learning model may include, for example, a deep neural network such as a convolutional neural network (CNN).

(Saliva)

Saliva contains cortisol that is a kind of stress hormone. It is known that, when getting stress, a cortisol content in the saliva increases. Accordingly, for example, when the cortisol content in saliva is higher than a predetermined threshold, it is possible to estimate that the arousal level of the target living body is high.

In addition, it is possible to estimate the arousal level of the target living body with use of, for example, an estimation model that estimates the arousal level of the target living body on the basis of the cortisol content in saliva. This estimation model is, for example, a model trained using, as teaching data, a cortisol content in saliva when the arousal level is apparently high. For example, in a case where a cortisol content in saliva is inputted, this estimation model estimates the arousal level of the target living body on the basis of the inputted cortisol content. This estimation model includes, for example, a neural network. This learning model may include, for example, a deep neural network such as a convolutional neural network (CNN).

Meanwhile, examples of motion information from which the arousal level of the target living body is derivable include information about facial expression, voice, blinking, breathing, or a reaction time for an action.

(Facial Expression)

It is known that eyebrows are knitted when thinking about something, and that zygomaticus major muscles hardly change when thinking about happy things. Thus, it is possible to estimate emotion or the arousal level in accordance with facial expression. Accordingly, for example, a face is photographed by a camera to estimate facial expression on the basis of thus-acquired moving image data, and it is possible to estimate whether the arousal level of the target living body is high or low, in accordance with the facial expression obtained by the estimation.

In addition, it is possible to estimate the arousal level of the target living body with use of, for example, an estimation model that estimates the arousal level of the target living body on the basis of moving image data acquired by photographing facial expression. This estimation model is, for example, a model trained using, as teaching data, moving image data acquired by photographing facial expression when the arousal level is apparently high. For example, in a case where moving image data acquired by photographing facial expression is inputted, this estimation model estimates the arousal level of the target living body on the basis of the inputted moving image data. This estimation model includes, for example, a neural network. This learning model may include, for example, a deep neural network such as a convolutional neural network (CNN).

(Voice)

It is known that voice changes in accordance with emotion or the arousal level similarly to facial expression. Accordingly, for example, voice data is acquired by a microphone, and it is possible to estimate whether the arousal level of the target living body is high or low, on the basis of the thus-acquired voice data.

In addition, it is possible to estimate the arousal level of the target living body with use of, for example, an estimation model that estimates the arousal level of the target living body on the basis of the voice data. This estimation model is, for example, a model trained using, as teaching data, voice data when the arousal level is apparently high. For example, in a case where voice data is inputted, this estimation model estimates the arousal level of the target living body on the basis of the inputted voice data. This estimation model includes, for example, a neural network. This learning model may include, for example, a deep neural network such as a convolutional neural network (CNN).

(Blinking)

It is known that blinking changes in accordance with emotion or the arousal level similarly to facial expression. Accordingly, for example, blinking is photographed by a camera to measure a frequency of blinking on the basis of thus-acquired moving image data, and it is possible to estimate whether the arousal level of the target living body is high or low, on the basis of the frequency of blinking obtained by the measurement. In addition, for example, the frequency of blinking is measured by an electrooculogram, and it is possible to estimate whether the arousal level of the target living body is high or low, in accordance with the frequency of blinking obtained by the measurement.

In addition, it is possible to estimate the arousal level of the target living body with use of, for example, an estimation model that estimates the arousal level of the target living body on the basis of moving image data acquired by photographing blinking or the electrooculogram. This estimation model is, for example, a model trained using, as teaching data, moving image data acquired by photographing blinking or an electrooculogram when the arousal level is apparently high. For example, in a case where moving image data acquired by photographing blinking or a electrooculogram is inputted, this estimation model estimates the arousal level of the target living body on the basis of the inputted moving image data or the inputted electrooculogram. This estimation model includes, for example, a neural network. This learning model may include, for example, a deep neural network such as a convolutional neural network (CNN).

(Breathing)

It is known that breathing changes in accordance with emotion or the arousal level similarly to facial expression. Accordingly, for example, a respiratory volume or a respiration rate is measured, and it is possible to estimate whether the arousal level of the target living body is high or low, on the basis of thus-acquired measurement data.

In addition, it is possible to estimate the arousal level of the target living body with use of, for example, an estimation model that estimates the arousal level of the target living body on the basis of the respiratory volume or the respiration rate. This estimation model is, for example, a model trained using, as teaching data, a respiratory volume or a respiration rate when the arousal level is apparently high. For example, in a case where a respiratory volume or a respiration rate is inputted, this estimation model estimates the arousal level of the target living body on the basis of the inputted respiratory volume or the inputted respiration rate. This estimation model includes, for example, a neural network. This learning model may include, for example, a deep neural network such as a convolutional neural network (CNN).

(Reaction Time for Action)

It is known that a processing time (reaction time) when a person processes a plurality of tasks in succession and dispersion of processing times (reaction times) depend on the arousal level of the person. Accordingly, for example, the processing time (reaction time) or the dispersion of the processing times (reaction times) is measured, and it is possible to estimate whether the arousal level of the target living body is high or low, on the basis of thus-acquired measurement data.

FIGS. 12 and 13 each illustrate, by way of a graph, time (reaction time) taken by a user to answer when the user solves a large number of questions in succession. FIG. 12 illustrates a graph at the time of solving questions of a relatively low difficulty level, and FIG. 13 illustrates a graph at the time of solving questions of a relatively high difficulty level. FIG. 14 illustrates a power spectrum density obtained by performing FFT (Fast Fourier Transform) on observation data of a brain wave (α-wave) of the user when the user solves a large number of low difficulty level questions in succession. FIG. 15 illustrates a power spectrum density obtained by performing FFT on observation data of a brain wave (α-wave) of the user when the user solves a large number of high difficulty level questions in succession. FIGS. 14 and 15 each illustrate a graph obtained by measuring a brain wave (α-wave) at a segment of about 20 seconds and performing FFT using an analysis window of about 200 seconds.

It is appreciated from FIGS. 12 and 13 that not only reaction time becomes longer, but also dispersion of the reaction times becomes larger at the time of solving high difficulty level questions, as compared with the time of solving low difficulty level questions. It is appreciated from FIGS. 14 and 15 that power of a brain wave (α-wave) around 0.01 Hz is larger and the power of a brain wave (α-wave) around 0.02 to 0.04 is smaller at the time of solving the high difficulty level questions, as compared with the time of solving the low difficulty level questions. As used herein, the power of the brain wave (α-wave) around 0.01 Hz is appropriately referred to as a "fluctuation in a slow (low-frequency band) brain wave (α-wave)".

FIG. 16 illustrates an example of a relationship between a task difference $\Delta tv$ [s] and a task difference $\Delta P$ [mV$^2$/Hz)$^2$/Hz]. The task difference $\Delta tv$ [s] is a task difference in dispersion (75% percentile-25% percentile) of reaction times of the user between the time of solving the high difficulty level questions and the time of solving the low difficulty level questions. The task difference $\Delta P$ [mV$^2$/Hz)$^2$/Hz] is a task difference in a peak value of power of the slow brain wave (α-wave) of the user between the time of solving the high difficulty level questions and the time of solving the low difficulty level questions. The task difference $\Delta tv$ [s] is a vector volume obtained by subtracting dispersion of reaction times of the user at the time of solving low difficulty level questions from dispersion of reaction times of the user at the time of solving the high difficulty level questions. The task difference $\Delta P$ is a vector volume obtained by subtracting a peak value of the power of the slow brain wave (α-wave) of the user at the time of solving the low difficulty level questions from a peak value of the power of the slow brain wave (α-wave) of the user at the time of solving the high difficulty level questions. It is to be noted that the kind of the dispersion of the reaction times is not limited to 75% percentile-25% percentile, and may be, for example, standard deviation.

FIG. 17 illustrates an example of a relationship between the task difference $\Delta tv$ [s] and a task difference $\Delta R$ [%]. The task difference $\Delta tv$ [s] is the task difference in the dispersion (75% percentile-25% percentile) of the reaction times of the user between the time of solving the high difficulty level questions and the time of solving the low difficulty level questions. The task difference $\Delta R$ [%] is a task difference in an accuracy rate for questions between the time of solving the high difficulty level questions and the time of solving the low difficulty level questions. The task difference $\Delta R$ is a vector volume obtained by subtracting the accuracy rate at the time of solving the low difficulty level questions from the accuracy rate at the time of solving the high difficulty level questions. It is to be noted that the kind of the dispersion of the reaction times is not limited to 75% percentile-25% percentile, and may be, for example, standard deviation.

In FIGS. 16 and 17, data for respective users are plotted, and features of the entirety of users are represented by a regression formula (regression line). In FIG. 16, the regression formula is represented by $\Delta P = a1 \times \Delta tv + b1$, and in FIG. 17, the regression formula is represented by $\Delta R = a2 \times \Delta tv + b2$.

A small task difference $\Delta tv$ in the dispersion of the reaction times means that the difference in the dispersion of the reaction times between the time of solving the high difficulty level questions and the time of solving the low difficulty level questions is small. It can be said that a user who has obtained such a result has a tendency in which, as the difficulty level of the questions becomes high, the task difference in dispersion of time periods for solving questions becomes smaller as compared with other users. Meanwhile, a large task difference $\Delta tv$ in the dispersion of the reaction times means that the difference in the dispersion of the reaction times between the time of solving the high difficulty level questions and the time of solving the low difficulty level questions is large. It can be said that a user who has obtained such a result has a tendency in which, as the difficulty level of the questions becomes high, the task difference in dispersion of time periods for solving questions becomes larger as compared with other users.

It is appreciated from FIG. 16 that, when the task difference $\Delta tv$ in the dispersion of the reaction times is small, the task difference $\Delta P$ in the peak value of the power of the slow brain wave (α-wave) becomes large, and that, when the task difference $\Delta tv$ in the dispersion of the reaction times is large, the task difference $\Delta P$ in the peak value of the power of the slow brain wave (α-wave) becomes small. It is appreciated from the above that a person who is able to answer even difficult questions within the same degree of reaction time as that for simple questions has a tendency in which the task difference $\Delta P$ in the peak value of the power of the slow brain wave (α-wave) becomes large. Conversely, it is appreciated that a person who has large dispersion of reaction times for difficult questions has a tendency in which the task difference $\Delta P$ in the peak value of the power of the slow brain wave (α-wave) does not vary so much regardless of the difficulty level of the questions.

It is appreciated from FIG. 17 that, when the task difference $\Delta tv$ in the dispersion of the reaction times is large, the task difference $\Delta R$ in the accuracy rate for questions becomes small, and that, when the task difference $\Delta tv$ in the dispersion of the reaction times is small, the task difference ΔR in the accuracy rate for questions becomes large. It is appreciated from the above that a person who has large dispersion of the reaction times for difficult questions has a tendency in which the task difference ΔR in the accuracy rate becomes small (i.e., the accuracy rate for difficult questions is lowered). Conversely, it is appreciated that a person who has small dispersion of the reaction times even for difficult questions has a tendency in which the task difference ΔR in the accuracy rate becomes large (i.e., is able to answer accurately even for difficult questions to the same degree as for simple questions).

It can be inferred from the above that, when the task difference Δtv in the dispersion of the reaction times is large, a cognitive capacity (cognitive resource) of the user is lower than a predetermined standard. In addition, it can be inferred that, when the task difference Δtv in the dispersion of the reaction times is small, the cognitive capacity of the user is higher than the predetermined standard. In a case where the cognitive capacity of the user is lower than the predetermined standard, the difficulty level of the questions may possibly be too high for the user. Meanwhile, in a case where the cognitive capacity of the user is higher than the predetermined standard, the difficulty level of questions may possibly be too low for the user.

FIG. 18 illustrates an example of a relationship between a task difference Δk [%] and the task difference ΔP [mV$^2$/Hz)$^2$/Hz]. The task difference Δk [%] is a task difference in an arousal level of the user between the time of solving the high difficulty level questions and the time of solving the low difficulty level questions. The task difference ΔP [mV$^2$/Hz)$^2$/Hz] is the task difference in the peak value of the power of the slow brain wave (α-wave) of the user between the time of solving the high difficulty level questions and the time of solving the low difficulty level questions. FIG. 19 illustrates an example of a relationship between the task difference Δk [%] and the task difference ΔR [%]. The task difference Δk [%] is the task difference in the arousal level of the user between the time of solving the high difficulty level questions and the time of solving the low difficulty level questions. The task difference ΔR [%] is the task difference in the accuracy rate for questions between the time of solving the high difficulty level questions and the time of solving the low difficulty level questions. The task difference Δk [%] is a vector volume obtained by subtracting the arousal level of the user at the time of solving the low difficulty level questions from the arousal level of the user at the time of solving the high difficulty level questions. The arousal level is obtained, for example, by using the above-described estimation model that estimates the arousal level with use of the brain wave.

In FIGS. 18 and 19, data for respective users are plotted, and features of the entirety of users are represented by a regression formula (regression line). In FIG. 18, the regression formula is represented by ΔP=a3×Δk+b3, and in FIG. 19, the regression formula is represented by ΔR=a4×Δk+b4.

It is appreciated from FIGS. 16 to 19 that the task difference Δtv in the dispersion of the reaction times and task difference Δk in the arousal level have a correspondence relationship. Accordingly, it is appreciated that it is possible to estimate the task difference Δk in the arousal level by measuring the task difference Δtv in the dispersion of the reaction times.

FIG. 20 illustrates an example of a relationship between the dispersion (75% percentile-25% percentile) tv [s] of the reaction times of the user at the time of solving the high difficulty level questions and the accuracy rate R [%] for questions at the time of solving the high difficulty level questions. In FIG. 20, data for respective users are plotted, and features of the entirety of users are represented by a regression formula (regression line). In FIG. 20, the regression formula is represented by R=a5×tv+b5.

FIG. 21 illustrates an example of a relationship between the arousal level k [%] of the user at the time of solving the high difficulty level questions and the accuracy rate R [%] for questions at the time of solving the high difficulty level questions. In FIG. 21, data for respective users are plotted, and features of the entirety of users are represented by a regression formula (regression line). In FIG. 21, the regression formula is represented by R=a6×k+b6.

It is appreciated from FIGS. 20 and 21 that the dispersion tv of the reaction times and the arousal level k have a correspondence relationship. Accordingly, it is appreciated that it is possible to estimate the arousal level k by measuring the dispersion tv of the reaction times.

2. About Comfort/Discomfort

Comfort/discomfort of a person is closely related to concentration of the person. A person in concentration is interested and concerned in an object on which the person is concentrated. Accordingly, it is possible to estimate an objective interest/concern degree (emotion) of the person by knowing comfort/discomfort of the person. It is possible to derive comfort/discomfort of the person on the basis of biological information or motion information acquired from the person who is in conversation with a communication partner or the communication partner (hereinafter referred to as a "target living body").

Examples of biological information from which comfort/discomfort of the target living body is derivable include information about a brain wave and sweating. In addition, examples of motion information from which the comfort/discomfort of the target living body is derivable include facial expression.

(Brain Wave)

It is known that it is possible to estimate comfort/discomfort of a person from a difference in an α-wave included in a brain wave between a left forehead and a right forehead. Accordingly, for example, an α-wave included in a brain wave obtained in the left forehead (hereinafter referred to as a "left-side α-wave") and an α-wave included in a brain wave obtained in the right forehead (hereinafter referred to as a "right-side α-wave") are compared with each other. In this case, it is possible to estimate that, when the left-side α-wave is lower than the right-side α-wave, the target living body feels comfort, and that, when the left-side α-wave is higher than the right-side α-wave, the target living body feels discomfort.

In addition, in estimating the comfort/discomfort of the target living body with use of the brain wave, it is possible to use an estimation model such as machine learning in place of deriving a difference in the α-wave included in the brain wave between the left forehead and the right forehead. This estimation model is, for example, a model trained using, as teaching data, an α-wave or a β-wave included in a brain wave when the target living body apparently feels comfort. For example, in a case where an α-wave or a β-wave included in a brain wave is inputted, this estimation model estimates the comfort/discomfort of the target living body on the basis of the inputted α-wave or the inputted β-wave. This estimation model includes, for example, a neural network. This learning model may include, for example, a deep neural network such as a convolutional neural network (CNN).

(Sweating)

Emotional sweating is sweating released from eccrine sweat glands when sympathetic nerves are strained due to a mental/psychological issue such as stress, tension, or anxiety. For example, a sweat sensor probe is attached to a palm or a sole, and sweating (emotional sweating) on the palm or the sole induced by various load stimuli is measured, which makes it possible to obtain a sympathetic sweat response (SSwR) as a signal voltage. When, in this signal voltage, a numeric value of a predetermined high-frequency component or a predetermined low-frequency component obtained from a left hand is higher than a numeric value of the predetermined high-frequency component or the predetermined low-frequency component obtained from a right hand, it is possible to estimate that the target living body feels comfort. In addition, when, in the signal voltage described above, the numeric value of the predetermined high-frequency component or the predetermined low-frequency component obtained from the left hand is lower than the numeric value of the predetermined high-frequency component or the predetermined low-frequency component obtained from the right hand, it is possible to estimate that the target living body feels discomfort. In addition, when, in this signal voltage, an amplitude value obtained from the left hand is higher than an amplitude value obtained from the right hand, it is possible to estimate that the target living body feels comfort. In addition, when, in the signal voltage described above, the amplitude value obtained from the left hand is lower than the amplitude value obtained from the right hand, it is possible to estimate that the target living body feels discomfort.

In addition, it is possible to estimate the arousal level of the target living body with use of, for example, an estimation model that estimates the arousal level of the target living body on the basis of the predetermined high-frequency component or the low-frequency component included in this signal voltage. This estimation model is, for example, a model trained using, as teaching data, the predetermined high-frequency component or the predetermined low-frequency component included in a signal voltage when the arousal level is apparently high. For example, in a case where the predetermined high-frequency component or the predetermined low-frequency component is inputted, this estimation model estimates the arousal level of the target living body on the basis of the inputted predetermined high-frequency component or the inputted predetermined low-frequency component. This estimation model includes, for example, a neural network. This learning model may include, for example, a deep neural network such as a convolutional neural network (CNN).

(Facial Expression)

It is known that eyebrows are knitted when feeling discomfort, and that zygomaticus major muscles hardly change when feeling comfort. Thus, it is possible to estimate comfort/discomfort in accordance with facial expression. Accordingly, for example, a face is photographed by a camera to estimate facial expression on the basis of thus-acquired moving image data, and it is possible to estimate the comfort/discomfort of the target living body in accordance with the facial expression obtained by the estimation.

In addition, it is possible to estimate the comfort/discomfort of the target living body with use of, for example, an estimation model that estimates the comfort/discomfort of the target living body on the basis of moving image data acquired by photographing facial expression. This estimation model is, for example, a model trained using, as teaching data, moving image data acquired by photographing facial expression when the arousal level is apparently high. For example, in a case where moving image data acquired by photographing facial expression is inputted, this estimation model estimates the comfort/discomfort of the target living body on the basis of the inputted moving image data. This estimation model includes, for example, a neural network. This learning model may include, for example, a deep neural network such as a convolutional neural network (CNN).

For example, the following literature describes a frequency component of a brain wave.

Wang, Xiao-Wei, Dan Nie, and Bao-Liang Lu. "EEG-based emotion recognition using frequency domain features and support vector machines." International conference on neural information processing. Springer, Berlin, Heidelberg, 2011.

For example, the following literature describes an estimation model using a brain wave.

Japanese Patent Application No. 2020-203058

For example, the following literatures describe sweating.

Jing Zhai, A. B. Barreto, C. Chin and Chao Li, "Realization of stress detection using psychophysiological signals for improvement of human-computer interactions," Proceedings. IEEE SoutheastCon, 2005, Ft. Lauderdale, FL, USA, 2005, pp. 415-420, doi: 10.1109/SECON.2005.1423280.

Boucsein, Wolfram. Electrodermal activity. Springer Science & Business Media, 2012. For example, the following literature describes the heart rate.

Veltman, J. A., and A. W. K. Gaillard. "Physiological indices of workload in a simulated flight task." Biological psychology 42.3 (1996): 323-342.

For example, the following literature describes heart rate variability intervals.

Appelhans, Bradley M., and Linda J. Luecken. "Heart rate variability as an index of regulated emotional responding." Review of general psychology 10.3 (2006): 229-240.

For example, the following literature describes a cortisol content in saliva.

Lam, Suman, et al. "Emotion regulation and cortisol reactivity to a social-evaluative speech task." Psychoneuroendocrinology 34.9 (2009): 1355-1362.

For example, the following literature describes facial expression.

Lyons, Michael J., Julien Budynek, and Shigeru Akamatsu. "Automatic classification of single facial images." IEEE transactions on pattern analysis and machine intelligence 21.12 (1999): 1357-1362.

For example, the following literature describes facial muscles.

Ekman, Paul. "Facial action coding system." (1977).

For example, the following literature describes a blinking frequency Chen, Siyuan, and Julien Epps. "Automatic classification of eye activity for cognitive load measurement with emotion interference." Computer methods and programs in biomedicine 110.2 (2013): 111-124.

For example, the following literature describes respiratory volume/respiration rate.

Zhang Q., Chen X., Zhan Q., Yang T., Xia S. Respiration-based emotion recognition with deep learning. Comput. Ind. 2017; 92-93:84-90. doi: 10.1016/j.compind.2017.04.005.

For example, the following literature describes a skin surface temperature.

Nakanishi R., Imai-Matsumura K. Facial skin temperature decreases in infants with joyful expression. Infant Behav. Dev. 2008; 31:137-144. doi: 10.1016/j.infbeh.2007.09.001.

For example, the following literature describes multimodal.

Choi J.-S., Bang J., Heo H., Park K. Evaluation of Fear Using Nonintrusive Measurement of Multimodal Sensors. Sensors. 2015; 15:17507-17533. doi: 10.3390/s150717507.

In the following, description is given of embodiments of an information processing system using an derivation algorithm of the arousal level or the comfort/discomfort described above.

3. First Embodiment

Configuration

Description is given of an information processing system 100 according to a first embodiment of the present disclosure. FIG. 1 illustrates a schematic configuration example of the information processing system 100. The information processing system 100 is a system that evaluates emotional information about the target living body on the basis of at least one of biological information or motion information acquired from the target living body. In the present embodiment, the target living body is a human. It is to be noted that, in the information processing system 100, the target living body is not limited to the human.

The information processing system 100 includes a plurality of electronic apparatuses 10. The plurality of electronic apparatuses 10 is coupled to each other to enable data transmission/reception via a network 30. The information processing system 100 further includes a plurality of biological sensors 20. The plurality of biological sensor 20 is assigned one to each of the electronic apparatuses 10, and each of the biological sensors 20 is coupled to the electronic apparatus 10. The network 30 is a wireless or wired communication means, and examples thereof include the Internet, a WAN (Wide Area Network), a LAN (Local Area Network), a public communication network, a dedicated line, and the like.

The biological sensor 20 may be, for example, a sensor of a type that comes in contact with the target living body or a sensor that is noncontact with the target living body. The biological sensor 20 is, for example, a sensor that acquires information (biological information) about at least one of a brain wave, sweating, a pulse wave, an electrocardiogram, a blood flow, a skin temperature, potential of facial muscles, eye potential, or a specific component contained in saliva. The biological sensor 20 may be, for example, a sensor that acquires information (motion information) about at least one of facial expression, voice, blinking, breathing, or a reaction time for an action. The biological sensor 20 may be, for example, a sensor that acquires information (biological information) about at least one of a brain wave or sweating. The biological sensor 20 may be, for example, a sensor that acquires information (motion information) about facial expression. The biological sensor 20 may be, for example, a sensor that acquires at least one piece of information of the above-described biological information or the above-described motion information. The biological sensor 20 outputs the acquired information (at least one piece of information of the above-described biological information or the above-described action information) to the electronic apparatus 10.

The electronic apparatus 10 includes, for example, a camera 11, a microphone 12, a sensor input receiver 13, a user input receiver 14, a signal processor 15, a storage section 16, an image signal generator 17a, a voice signal generator 17b, an image display section 18a, and a speaker 18b, as illustrated in FIG. 2. The camera 11 corresponds to a specific example of an "imaging section" of the present disclosure. The signal processor 15 corresponds to a specific example of each of an "estimation section", a "first estimation section", a "second estimation section", an "acquisition section", and an "association section" of the present disclosure. The storage section 16 corresponds to a specific example of a "storage section" of the present disclosure. The image display section 18a corresponds to a specific example of a "display section" of the present disclosure.

The camera 11 includes, for example, a CCD (Charge Coupled Device) image sensor, a CMOS (Complementary Metal Oxide Semiconductor) image sensor, or the like. The camera 11 performs imaging in accordance with control by the signal processor 15, and outputs image data acquired by imaging to the signal processor 15. The camera 11 obtains a moving image of the face of a user (target living body) who visually recognizes display of the electronic apparatus 10 via a camera lens 11b provided adjacent to a display surface 10a. The camera lens 11b is disposed, for example, around a middle of an upper end side of the display surface 10a. The microphone 12 includes, for example, a microphone that detects voice. The microphone 12 performs voice detection in accordance with control by the signal processor 15, and outputs voice data acquired by the voice detection to the signal processor 15.

The sensor input receiver 13 receives an input from the biological sensor 20, and outputs the input to the signal processor 15. The input from the biological sensor 20 includes at least one of the above-described biological information or the above-described action information. The sensor input receiver 13 includes, for example, an interface that is able to communicate with the biological sensor 20. The user input receiver 14 receives an input from the user, and outputs the input to the signal processor 15. Examples of the input from the user include attribute information (e.g., a name or the like) about the target living body, and an emotion estimation start instruction. The user input receiver 14 includes, for example, an input interface such as a keyboard, a mouse, or a touch panel.

The storage section 16 is, for example, a volatile memory such as a DRAM (Dynamic Random Access Memory), or a non-volatile memory such as an EEPROM (Electrically Erasable Programmable Read-Only Memory) or a flash memory. An information processing program 16a for estimating emotion of the target living body is stored in the storage section 16. Furthermore, an identifier 16b, emotional information 16c, and a context 16d that are acquired by processing by the information processing program 16a are stored in the storage section 16. Details of the processing in the information processing program 16a are described in detail later.

The identifier 16b is numeric value data for identifying the target living body, and is, for example, an identification number assigned to each target living body. The identifier 16b is generated, for example, at a timing when the target living body inputs the attribute information about the target living body. The emotional information 16c is information about emotion derived on the basis of an input (detection signal) from the biological sensor 20. The emotional information 16c is, for example, numeric value data about at least one of an arousal level or comfort/discomfort that changes over time, as illustrated in FIG. 3.

The context 16d is information about at least one of motion or conversation of the target living body. The context 16d is, for example, information about at least one of motion or conversation of at least one of respective users of the plurality of electronic apparatuses coupled to the network 30. The context 16d is, for example, information about the target living body's line of sight or information about voice of the target living body, as illustrated in FIG. 3. It is possible to derive the information about the target living body's line of sight from the image data acquired by the camera 11, and the information about the target living body's line of sight corresponds to a non-voice context in an imaging period (sensing period) by the camera 11. It is possible to derive the information about the voice of the target living body from the voice data acquired by the microphone 12, and the information about the voice of the target living body corresponds to a voice context in a voice detection period (sensing period) by the microphone 12.

The image signal generator 17a generates an image signal for displaying the image data inputted from the signal processor 15, and outputs the image signal to the image display section 18a. The image display section 18a displays an image on the basis of the image signal inputted from the image signal generator 17a. The image display section 18a displays the emotional information 16c (at least one of the above-described arousal level or the above-described comfort/discomfort) about the target living body. The voice signal generator 17b generates a voice signal for outputting the voice data inputted from the signal processor 15, and outputs the voice signal to the speaker 18b. The speaker 18b outputs voice on the basis of the voice signal inputted from the voice signal generator 17b.

The signal processor 15 includes, for example, a processor. The signal processor 15 executes the information processing program 16a stored in the storage section 16. A function of the signal processor 15 is implemented, for example, by executing the information processing program 16a by the signal processor 15. The signal processor 15 executes a series of processing necessary for estimation of the emotion of the target living body.

The signal processor 15 estimates the emotional information 16c (at least one of the above-described arousal level or the above-described comfort/discomfort) about the target living body on the basis of at least one of the above-described biological information or the above-described motion information about the target living body acquired by the biological sensor 20. The signal processor 15 stores, in the storage section 16, the emotional information 16c acquired by estimation. The signal processor 15 generates the identifier 16b of the target living body, and stores, in the storage section 16, the generated identifier 16b and the emotional information 16c acquired by estimation in association with each other.

For example, it is assumed that a person A, a person B, and a person C each use the electronic apparatus 10 coupled to the network 30. In this case, the electronic apparatus 10 (signal processor 15) used by the person C acquires the emotional information 16c about the person A and the identifier 16b of the person A from the electronic apparatus 10 used by the person A. Furthermore, the electronic apparatus 10 (signal processor 15) used by the person C acquires the emotional information 16c about the person B and the identifier 16b of the person B from the electronic apparatus 10 used by the person B. Furthermore, the electronic apparatus 10 (signal processor 15) used by the person C uses the biological sensor 20 coupled to the electronic apparatus 10 used by the person C to acquire the emotional information about the person C and acquire the identifier 16b of the person C.

In the electronic apparatus 10 used by the person C, the signal processor 15 converts, for example, each of the emotional information 16c about the person A, the emotional information 16c about the person B, and the emotional information 16c about the person C into graphical emotional information. The signal processor 15 generates, for example, image data that represents the emotional information 16c about the person A, the emotional information 16c about the person B, and the emotional information 16c about the person C by a graph with a horizontal axis as time and a vertical axis as emotional information. In the electronic apparatus 10 used by the person C, the image display section 18a generates an image signal based on the image data, including the graphical emotional information, generated by the signal processor 15, and outputs the image signal to the image display section 18a. The image display section 18a displays, for example, the emotional information 16c about the person A, the emotional information 16c about the person B, and the emotional information 16c about the person C together on the display surface 10a, as illustrated in FIG. 3.

The signal processor 15 acquires, for example, the non-voice context 16d in the imaging period (sensor period) by the camera 11 on the basis of the image data (moving image data) acquired by the camera 11. The signal processor 15 acquires, for example, information about the target living body's line of sight on the basis of the image data (moving image data) acquired by the camera 11. The signal processor 15 stores, in the storage section 16, the identifier 16b of the target living body and the acquired non-voice context 16d (e.g., information about the target living body's line of sight) in association with each other.

For example, on the basis of moving image data a1, the signal processor 15 detects the gaze position of the target living body on the display surface 10a from the direction of eyeballs of the target living body included in the moving image data a1. As a result, when the gaze position of the target living body is within a display window of a moving image showing a user of another electronic apparatus 10 on the display surface 10a, the signal processor 15 generates, as data of the target living body's line of sight, data meaning that the target living body is gazing at the user of the other electronic apparatus 10. The signal processor 15 stores, in the storage section 16, the generated data of the target living body's line of sight as the non-voice context 16d together with the identifier 16b of the target living body.

For example, it is assumed that the person A, the person B, and the person C each use the electronic apparatus 10 coupled to the network 30. In this case, in the electronic apparatus 10 used by the person A, the camera 11 acquires moving image data of the face of the person A (hereinafter referred to as "moving image data a1"), and outputs the moving image data a1 to the signal processor 15. The signal processor 15 detects the gaze position of the person A on the display surface 10a from the direction of the eyeballs of the person A included in the moving image data a1 on the basis of the moving image data a1. As a result, when the gaze position of the person A is within a display window 10a-2 of a moving image showing the person B on the display surface 10a, the signal processor 15 generates, as data of the person A's line of sight, data meaning that the person A is gazing at the person B. In addition, when the gaze position of the person A is within a display window 10a-3 of a moving image showing the person C on the display surface 10*a*, the signal processor 15 generates, as data of the person A's line of sight, data meaning that the person A is gazing at the person C. The signal processor 15 stores, in the storage section 16, the generated data of the person A's line of sight as the non-voice context 16*d* together with the identifier 16*b* of the person A. Furthermore, the signal processor 15 transmits the identifier 16*b* of the person A and the non-voice context 16*d* to the electronic apparatuses 10 of the person B and the person C via a communication section 19 and the network 30.

In addition in the electronic apparatus 10 used by the person B, the camera 11 acquires moving image data of the face of the person B (hereinafter referred to as "moving image data a2"), and outputs the moving image data a2 to the signal processor 15. The signal processor 15 detects the gaze position of the person B on the display surface 10*a* from the direction of the eyeballs of the person B included in the moving image data a2 on the basis of the moving image data a2. As a result, when the gaze position of the person B is within a display window 10*a*-1 of a moving image showing the person A on the display surface 10*a*, the signal processor 15 generates, as data of the person B's line of sight, data meaning that the person B is gazing at the person A. In addition, when the gaze position of the person B is within the display window 10*a*-3 of the moving image showing the person C on the display surface 10*a*, the signal processor 15 generates, as data of the person B's line of sight, data meaning that the person B is gazing at the person C. The signal processor 15 stores, in the storage section 16, the generated data of the person B's line of sight as the non-voice context 16*d* together with the identifier 16*b* of the person B. Furthermore, the signal processor 15 transmits the identifier 16*b* of the person B and the non-voice context 16*d* to the electronic apparatuses 10 of the person A and the person C via the communication section 19 and the network 30.

In addition, in the electronic apparatus 10 used by the person C, the camera 11 acquires moving image data of the face of the person C (hereinafter referred to as "moving image data a3"), and outputs the moving image data a3 to the signal processor 15. The signal processor 15 detects the gaze position of the person C on the display surface 10*a* from the direction of the eyeballs of the person C included in the moving image data a3 on the basis of the moving image data a3. As a result, when the gaze position of the person C is within the display window 10*a*-1 of the moving image showing the person A on the display surface 10*a*, the signal processor 15 generates, as data of the person C's line of sight, data meaning that the person C is gazing at the person A. In addition, when the gaze position of the person C is within the display window 10*a*-2 of the moving image showing the person B on the display surface 10*a*, the signal processor 15 generates, as data of the person C's line of sight, data meaning that the person C is gazing at the person B. The signal processor 15 stores, in the storage section 16, the generated data of the person C's line of sight as the non-voice context 16*d* together with the identifier 16*b* of the person C. Furthermore, the signal processor 15 transmits the identifier 16*b* of the person C and the non-voice context 16*d* to the electronic apparatuses 10 of the person B and the person C via a communication section 19 and the network 30.

In the electronic apparatus 10 used by the person C, the signal processor 15 acquires the identifier 16*b* of the person A and the non-voice context 16*d* of the person A from the electronic apparatus 10 used by the person A. In the electronic apparatus 10 used by the person C, the signal processor 15 further acquires the identifier 16*b* of the person B and the non-voice context 16*d* of the person B from the electronic apparatus 10 used by the person B. The signal processor 15 stores, in the storage section 16, the identifier 16*b* of the person A, the non-voice context 16*d* of the person A, the identifier 16*b* of the person B, and the non-voice context 16*d* of the person B. In the electronic apparatus 10 used by the person C, the signal processor 15 converts each of the non-voice contexts 16*d* of the person A, the person B, and the person C into, for example, graphical data as illustrated in FIG. 3. In the electronic apparatus 10 used by the person C, the image signal generator 17*a* generates an image signal based on image data including the emotional information 16*c* about the person A, the emotional information 16*c* about the person B, the emotional information 16*c* about the person C, and the graphical non-voice contexts 16*d* of the person A, the person B, and the person C, and outputs the image signal to the image display section 18*a*. The image display section 18*a* displays, for example, the emotional information 16*c* about the person A, the emotional information 16*c* about the person B, the emotional information 16*c* about the person C, and the graphical non-voice contexts 16*d* of the person A, the person B, and the person C together on the display surface 10*a*, as illustrated in FIG. 3. FIG. 3 exemplifies, as graphical display of the non-voice contexts 16*d* (data of lines of sight), a bar graph representing a period of time during gazing at a communication partner in colors.

The signal processor 15 acquires, for example, the voice context 16*d* in the voice detection period (sensing period) by the microphone 12 on the basis of voice data acquired by the microphone 12. The signal processor 15 acquires, for example, information about voice of the target living body on the basis of the voice data acquired by the microphone 12. The signal processor 15 stores, in the storage section 16, the identifier 16*b* of the target living body and the acquired voice context 16*d* (e.g., information about the voice of the target living body) in association with each other.

It is assumed that, for example, the person A, the person B, and the person C each use the electronic apparatus 10 coupled to the network 30. In this case, in the electronic apparatus 10 used by the person A, the microphone 12 acquires voice data of the person A (hereinafter referred to as "voice data a2"), and outputs the voice data a2 to the signal processor 15. The signal processor 15 stores, in the storage section 16, the acquired voice data a2 of the person A as the voice context 16*d* together with the identifier 16*b* of the person A. Furthermore, the signal processor 15 transmits the identifier 16*b* of the person A and the voice context 16*d* to the electronic apparatuses 10 of the person B and the person C via the communication section 19 and the network 30.

In addition, in the electronic apparatus 10 used by the person B, the microphone 12 acquires voice data of the person B (hereinafter referred to as "voice data b2"), and outputs the voice data b2 to the signal processor 15. The signal processor 15 stores, in the storage section 16, the acquired voice data b2 of the person B as the voice context 16*d* together with the identifier 16*b* of the person B. Furthermore, the signal processor 15 transmits the identifier 16*b* of the person B and the voice context 16*d* to the electronic apparatuses 10 of the person A and the person C via the communication section 19 and the network 30.

In addition, in the electronic apparatus 10 used by the person C, the microphone 12 acquires voice data of the person C (hereinafter referred to as "voice data c2"), and outputs the voice data c2 to the signal processor 15. The signal processor 15 stores, in the storage section 16, the acquired voice data c2 of the person C as the voice context 16d together with the identifier 16b of the person C. Furthermore, the signal processor 15 transmits the identifier 16b of the person C and the voice context 16d to the electronic apparatuses 10 of the person A and the person B via the communication section 19 and the network 30.

In the electronic apparatus 10 used by the person C, the signal processor 15 acquires the identifier 16b of the person A and the voice context 16d of the person A from the electronic apparatus 10 used by the person A. In the electronic apparatus 10 used by the person C, the signal processor 15 further acquires the identifier 16b of the person B and the voce context 16d of the person B from the electronic apparatus 10 used by the person B. The signal processor 15 stores, in the storage section 16, the identifier 16b of the person A, the voice context 16d of the person A, the identifier 16b of the person B, and the voice context 16d of the person B. In the electronic apparatus 10 used by the person C, the signal processor 15 converts each of the voice contexts 16d of the person A, the person B, and the person C into, for example, graphical data as illustrated in FIG. 3. In the electronic apparatus 10 used by the person C, the image signal generator 17a generates an image signal based on image data including the emotional information 16c about the person A, the emotional information 16c about the person B, the emotional information 16c about the person C, and the graphical voice contexts 16d of the person A, the person B, and the person C, and outputs the image signal to the image display section 18a. The image display section 18a displays, for example, the emotional information 16c about the person A, the emotional information 16c about the person B, the emotional information 16c about the person C, and the graphical voice contexts 16d of the person A, the person B, and the person C together on the display surface 10a, as illustrated in FIG. 3. FIG. 3 exemplifies, as graphical display of the voice contexts 16d (voice data), a bar graph representing a period of time during speech in colors.

In the electronic apparatus 10 used by the person C, the signal processor 15 may generate a message 10b to the person C on the basis of the voice context 16d (voice data), the non-voice context 16d (data of the line of sight), and the emotional information 16c. For example, it is assumed that, when the person C is speaking in the voice context 16d (voice data), the person A is gazing at the person C in the non-voice context 16d (data of the line of sight), and the emotional information 16c about the person A has a high value. In this case, it is conceivable that the person A has some kind of interest and concern in the person C. Accordingly, the signal processor 15 may generate, for example, as the message 10b, for example, text data such as "Person A is looking at you. Try to look at person A and talk".

It is to be noted that, in the electronic apparatus 10 used by the person C, the signal processor 15 may calculate the number of times the person A has gazed at the person C and total time the person A has gazed at the person C on the basis of the non-voice context 16d (data of the line of sight). In this case, when the number of times the person A has gazed at the person C or the total time the person A has gazed at the person C exceeds a predetermined threshold, the signal processor 15 may generate, for example, as the message 10b, for example, text data such as "Person A seems interested and concerned in you. Try to talk to person A". In addition, the signal processor 15 may calculate the number of times the person A has gazed at the person C or the total time the person has gazed at the person C, and the number of times the person B has gazed at the person C or the total time the person B has gazed at the person C, and store them in the storage section 24.

In the electronic apparatus 10 used by the person C, the image signal generator 17a may generate image data including the message 10b generated by the signal processor 15 and output the image data to the image display section 18a. In this case, the image display section 18a may display the message 10b, for example, at a position close to a camera lens 11a on the display surface 10a, as illustrated in FIG. 3. In this case, the person C is able to visually recognize the message 10b only by turning the person C's line of sight to the vicinity of the camera lens 11a for visual recognition. Accordingly, it is not necessary for the person C to move in unnatural ways such as averting the person C's eyes to visually recognize the message 10b. This consequently makes it possible for the person C to visually recognize the message 10b while making a natural conversation with the person A or the person B, and to make a motion or a conversation based on the message 10b.

In the electronic apparatus 10 used by the person C, the voice signal generator 17b may generate voice data corresponding to the message 10b generated by the signal processor 15 and output the voice data to the speaker 18b. In this case, in a case where the speaker 18b includes an earphone, a bone conduction speaker, or the like, the speaker 18b is able to output voice generated on the basis of the voice data only to the person C without allowing the person A and the person B to hear the voice. Accordingly, it is not necessary for the person C to move in unnatural ways such as averting the person C's eyes to obtain the message 10b. This consequently makes it possible for the person C to hear the message 10b from the speaker 18b while making a natural conversation with the person A or the person B, and to make a motion or a conversation based on the heard message 10b.

Effects

Next, description is given of effects of the information processing system 100.

In the present embodiment, the emotional information 16c about the target living body is estimated on the basis of information (at least one of the biological information or the motion information) about the target living body acquired by the biological sensor 20, and is displayed on the display surface 10a. Accordingly, for example, in a case where the target living body is a communication partner, the user is able to infer an element necessary for relationship building with the partner on the basis of the emotional information 16c about the partner. Herein, the emotional information 16c about the partner is objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. In addition, for example, in a case where the target living body is the user oneself, the user is able to infer the element necessary for relationship building with the partner on the basis of the emotional information 16c about the user oneself Herein, the emotional information about the user oneself is objective information acquired in a process of mutual communication. Accordingly, it is possible to perform more accurate inference, as compared with a case of inferring the element necessary for relationship building with the partner on the basis of the action history of the partner, and preference information and attribute information about the partner. This consequently makes it possible to more accurately determine mutual congeniality.

In the present embodiment, the non-voice context 16*d* in the sensing period by the biological sensor 20 and the emotional information 16*c* are displayed. Accordingly, for example, in a case where the target living body is a communication partner, the user is able to infer the element necessary for relationship building with the partner on the basis of the non-voice context 16*d* of the partner and the emotional information 16*c* about the partner. Herein, the non-voice context 16*d* of the partner and the emotional information 16*c* about the partner are objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. In addition, for example, in a case where the target living body is the user oneself, the user is able to infer the element necessary for relationship building with the partner on the basis of the non-voice context 16*d* of the user oneself and the emotional information 16*c* about the user oneself Herein, the non-voice context 16*d* of the user oneself and the emotional information about the user oneself are objective information acquired in a process of mutual communication. Accordingly, it is possible to perform more accurate inference, as compared with a case of inferring the element necessary for relationship building with the partner on the basis of the action history of the partner, and preference information and attribute information about the partner. This consequently makes it possible to more accurately determine mutual congeniality.

In the present embodiment, the camera 11 is provided that obtains a moving image of the face of the user via the camera lens 11*b* provided adjacent to the display surface 10*a*, and the context 16*d* is displayed at a position close to the camera lens 11*b* on the display surface 10*a*. Accordingly, the user is able to visually recognize the message 10*b* only by turning the user's line of sight to the vicinity of the camera lens 11*a* for visual recognition. As a result, it is not necessary for the user to move in unnatural ways such as averting the user's eyes to visually recognize the message 10*b*. This consequently makes it possible for the user to visually recognize the message 10*b* while having a natural conversation with another user, and to make a motion or a conversation based on the message 10*b*.

In the present embodiment, the emotional information 16*c* is displayed on the display surface 10*a*, and the voice context 16*d* in the sensing period by the biological sensor 20 is graphically displayed on the display surface 10*a*. Accordingly, for example, in a case where the target living body is a communication partner, the user is able to infer the element necessary for relationship building with the partner on the basis of the voice context 16*d* of the partner and the emotional information 16*c* about the partner. Herein, the voice context 16*d* of the partner and the emotional information 16*c* about the partner are objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. In addition, for example, in a case where the target living body is the user oneself, the user is able to infer the element necessary for relationship building with the partner on the basis of the voice context 16*d* of the user oneself and the emotional information 16*c* about the user oneself Herein, the voice context 16*d* of the user oneself and the emotional information about the user oneself are objective information acquired in a process of mutual communication. Accordingly, it is possible to perform more accurate inference, as compared with a case of inferring the element necessary for relationship building with the partner on the basis of the action history of the partner, and preference information and attribute information about the partner. This consequently makes it possible to more accurately determine mutual congeniality.

In the present embodiment, the emotional information 16*c* about oneself is estimated on the basis of at least one of the biological information or the motion information about oneself acquired by the biological sensor 20 coupled to the electronic apparatus 10 used by oneself. Furthermore, the emotional information 16*c* about another user is estimated on the basis of at least one of the biological information or the motion information about the other user acquired by the biological sensor 20 coupled to the electronic apparatus 10 used by the other user. Then, the emotional information 16*c* about oneself and the emotional information 16*c* about the other user are displayed together on the display surface 10*a*. This makes it possible for oneself to infer the element necessary for relationship building with a partner on the basis of both the emotional information 16*c* about oneself and the emotional information 16*c* about the other user. Herein, both the emotional information 16*c* about oneself and the emotional information 16*c* about the other user are objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner.

In the present embodiment, the non-voice context 16*d* in the sensing period by the biological sensor 20 coupled to the electronic apparatus 10 used by oneself is referred to as a first context. In the present embodiment, the non-voice context 16*d* in the sensing period by the biological sensor 20 that is coupled to the biological sensor 20 coupled to the electronic apparatus 10 used by another user is referred to as a second context. In the present embodiment, the emotional information 16*c* about oneself acquired by the electronic apparatus 10 used by oneself is referred to as first emotional information, and the emotional information 16*c* about the other user acquired by the electronic apparatus 10 used by the other user is referred to as second emotional information. In this case, the first context, the second context, the first emotional information, and the second emotional information are displayed together on the display surface 10*a*. This makes it possible for oneself to infer the element necessary for relationship building with the partner on the basis of these pieces of information. Herein, these pieces of information are objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. This consequently makes it possible to more accurately determine mutual congeniality.

In the present embodiment, the emotional information 16c about the target living body is estimated on the basis of information (at least one of biological information or motion information) about the target living body acquired by the biological sensor 20. Furthermore, in the present embodiment, the emotional information 16c about the target living body and the context 16d in the sensing period by the biological sensor 20 are associated with each other. Accordingly, for example, in a case where the target living body is a communication partner, the user is able to infer the element necessary for relationship building with the partner on the basis of the emotional information 16c about the partner. Herein, the emotional information 16c about the partner is objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. In addition, for example, in a case where the target living body is the user oneself, the user is able to infer the element necessary for relationship building with the partner on the basis of the emotional information 16c about the user oneself. Herein, the emotional information 16c about the user oneself is objective information acquired in a process of mutual communication. Accordingly, it is possible to perform more accurate inference, as compared with a case of inferring the element necessary for relationship building with the partner on the basis of the action history of the partner, and preference information and attribute information about the partner. This consequently makes it possible to more accurately determine mutual congeniality.

In the present embodiment, the emotional information 16c about the target living body and the non-voice context 16d are displayed together on the display surface 10a. Accordingly, for example, in a case where the target living body is a communication partner, the user is able to infer the element necessary for relationship building with the partner on the basis of the emotional information 16c about the partner and the non-voice context 16d. Herein, the emotional information 16c about the partner and the non-voice context 16d are objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. In addition, for example, in a case where the target living body is the user oneself, the user is able to infer the element necessary for relationship building with the partner on the basis of the emotional information 16c about the user oneself and the non-voice context 16d. Herein, the emotional information 16c about the user oneself and the non-voice context 16d are objective information acquired in a process of mutual communication. Accordingly, it is possible to perform more accurate inference, as compared with a case of inferring the element necessary for relationship building with the partner on the basis of the action history of the partner, and preference information and attribute information about the partner. This consequently makes it possible to more accurately determine mutual congeniality.

In the present embodiment, the emotional information 16c about the target living body and the voice context 16d are displayed together on the display surface 10a. Accordingly, for example, in a case where the target living body is a communication partner, the user is able to infer the element necessary for relationship building with the partner on the basis of the emotional information 16c about the partner and the voice context 16d. Herein, the emotional information 16c about the partner and the non-voice context 16d are objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. In addition, for example, in a case where the target living body is the user oneself, the user is able to infer the element necessary for relationship building with the partner on the basis of the emotional information 16c about the user oneself and the voice context 16d. Herein, the emotional information 16c about the user oneself and the voice context 16d are objective information acquired in a process of mutual communication. Accordingly, it is possible to perform more accurate inference, as compared with a case of inferring the element necessary for relationship building with the partner on the basis of the action history of the partner, and preference information and attribute information about the partner. This consequently makes it possible to more accurately determine mutual congeniality.

4. Modification Examples of First Embodiment

Next, description is given of modification examples of the information processing system 100 according to the embodiment described above.

Modification Example A

In the information processing system 100 according to the embodiment described above, the biological sensor 20, the camera 11, the image display section 18a, and the speaker 18b may be provided in, for example, a device such as eyeglasses. In such a case, for example, it is possible to derive the line of sight accurately or to prevent voice from the speaker 18b from being picked up by the microphone 12.

Modification Example B

In the information processing system 100 according to the embodiment described above, communication may be carried out only between two electronic apparatuses 10 coupled to the network 30. In such a case, in the electronic apparatus 10 used by oneself, the signal processor 15 acquires the emotional information 16c about oneself, and the identifier 16b of oneself. The signal processor 15 further acquires, from the electronic apparatus 10 used by a communication partner, the identifier 16b of the partner and the emotional information 16c about the partner.

In the electronic apparatus 10 used by oneself, the signal processor 15 converts, for example, each of the emotional information 16c about oneself and the emotional information 16c about the partner into graphical emotional information. The signal processor 15 generates, for example, image data that represents the emotional information 16c about oneself and the emotional information 16c about the partner by a graph with a horizontal axis as time and a vertical axis as emotional information. In the electronic apparatus 10 used by oneself, the image display section 18a generates an image signal based on the image data, including the graphical emotional information, generated by the signal processor 15, and outputs the image signal to the image display section 18*a*. The image display section 18*a* displays, for example, the emotional information 16*c* about oneself and the emotional information 16*c* about the partner together on the display surface 10*a*, as illustrated in FIG. 4.

The signal processor 15 may calculate, for example, synchronization between the emotional information 16*c* about oneself and the emotional information 16*c* about the partner and generate image data including a result of the calculation. In this case, the image display section 18*a* generates an image signal based on image data, including a result of calculation of synchronization, generated by the signal processor 15, and outputs the image signal to the image display section 18*a*. The image display section 18*a* displays, for example, the result of calculation of synchronization on the display surface 10*a*, as illustrated in FIG. 4.

The signal processor 15 may store, in the storage section 16, the emotional information 16*c* about oneself and the emotional information 16*c* about the partner in association with each other. The signal processor 15 may further store, in the storage section 16, for example, the result of calculation of synchronization described above. In such a case, the user is able to review suitability of a user's own method of communication with the partner on the basis of the emotional information 16*c* about oneself, the emotional information 16*c* about the partner, and the result of calculation of synchronization stored in the storage section 16. The user is able to know whether or not the partner's words are compliments or know what the partner is interested in, for example, by watching synchronization between the emotional information 16*c* about the user oneself and the emotional information 16*c* about the partner.

Modification Example C

The information processing system 100 according to the embodiment described above and the modification examples thereof is applicable to, for example, group interaction, dating, matchmaking, employee training, an online game, and the like.

For example, it is assumed that the information processing system 100 according to the embodiment described above and the modification examples thereof is applied to such a cooperative online game that the user teams up with a large number of unspecified persons online to clear quests. In this case, the image display section 18*a* may generate, for example, an image signal based on image data, including a game screen, and graphical emotional information about team members, generated by the signal processor 15, and output the image signal to the image display section 18*a*. In this case, seeing timings of ups and downs of emotions of the members makes it possible for each of the members to know a common point between scenes where the members are having fun or compatibility of cooperation in clearing quests.

5. Second Embodiment

Configuration

Next, description is given of an information processing system 200 according to a second embodiment of the present disclosure. FIG. 5 illustrates a schematic configuration example of the information processing system 200. The information processing system 200 corresponds to the information processing system 100 according to the embodiment described above and the modification examples thereof in which a server apparatus 50 coupled to a plurality of electronic apparatuses 40 by the network 30 may include a program or an estimation model for executing a series of processing for deriving the emotional information 16*c*.

For example, as illustrated in FIG. 6, the electronic apparatus 40 corresponds to the electronic apparatus 10 according to the embodiment described above and the modification examples thereof in which an information processing program 16*e* is stored in the storage section 16 in place of the information processing program 16*a*. The information processing program 16*e* is a program for executing of processing, except for a series of processing for deriving the emotional information 16*c*, of a series of processing to be executed by the information processing program 16*a*.

For example, as illustrated in FIG. 7, the server apparatus 50 includes a communication section 51, a signal processor 52, and a storage section 53. The communication section 51 is a device that communicates with the plurality of electronic apparatuses 40 via the network 30.

The signal processor 52 includes, for example, a processor. The signal processor 52 executes the information processing program 16*e* stored in the storage section 53. A function of the signal processor 52 is implemented, for example, by executing the information processing program 16*e* by the signal processor 52. The signal processor 52 executes the series of processing for deriving the emotional information 16*c*.

The signal processor 52 estimates the emotional information 16*c* (at least one of the above-described arousal level or the above-described comfort/discomfort) about the target living body on the basis of at least one of the above-described biological information or the above-described motion information inputted from each of the electronic apparatuses 40. The signal processor 52 transmits the emotional information 16*c* acquired by estimation to the electronic apparatus 40 via the communication section 51 and the network 30. The signal processor 52 stores, in the storage section 53, the identifier 16*b* inputted from the electronic apparatus 40 and the emotional information 16*c* acquired by estimation in association with each other. The signal processor 52 transmits the emotional information 16*c* to the electronic apparatus 40 corresponding to the identifier 16*b*. The signal processor 52 stores, in the storage section 53, the identifier 16*b* and the context 16*d* inputted from the electronic apparatus 40 in association with each other. The signal processor 52 transmits, to the electronic apparatus 40, the identifier 16*b* and the context 16*d* read from the storage section 53 in association with each other.

Thus, in the present modification example, the series of processing for deriving the emotional information 16*c* is executed by the server apparatus 50. Accordingly, it is not necessary to provide, in each of the electronic apparatuses 40, a program or an estimation model that executes the series of processing for deriving the emotional information 16*c*. This consequently makes it possible to share, by the plurality of electronic apparatuses 40, the program or the estimation model provided in the server apparatus 50. The program or the estimation model executes the series of processing for deriving the emotional information 16*c*.

6. Third Embodiment

Description is given of an information processing device 300 according to a third embodiment of the present disclosure. FIG. 8 illustrates a schematic configuration example of the information processing device 300. The information processing device 300 is a system that estimates emotional information about the target living body on the basis of at least one of biological information or motion information acquired from the target living body. In the present embodiment, the target living body is a human. It is to be noted that, in the information processing device 300, the target living body is not limited to the human.

The information processing device 300 includes a plurality of (e.g., two) devices 310, the signal processor 15 coupled to the plurality of (e.g., two) devices, the user input receiver 14, and the storage section 16. Each of the devices 310 is, for example, a device such as eyeglasses, and executes, by control by the signal processor 15, an operation similar to those of the electronic apparatus 10 according to the embodiment described above and the modification examples thereof, and the electronic apparatus 40 according to the embodiment described above and the modification examples thereof. In other words, in the present embodiment, one information processing device 300 is shared by a plurality of users.

Each of the devices 310 includes, for example, the camera 11, the microphone 12, the sensor input receiver 13, the image signal generator 17*a*, the image display section 18*a*, the voice signal generator 17*b*, and the speaker 18*b*. For example, one biological sensor 20 is mounted in each of the devices 310.

In the present embodiment, as with the embodiments described above and the modification examples thereof, the emotional information 16*c* about the target living body is estimated on the basis of information (at least one of biological information or motion information) about the target living body acquired by the biological sensor 20, and is displayed on the display surface of the image display section 18*a*. Accordingly, for example, in a case where the target living body is a communication partner, the user is able to infer the element necessary for relationship building with the partner on the basis of the emotional information 16*c* about the partner. Herein, the emotional information 16*c* about the partner is objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. In addition, for example, in a case where the target living body is the user oneself, the user is able to infer the element necessary for relationship building with the partner on the basis of the emotional information 16*c* about the user oneself Herein, the emotional information 16*c* about the user oneself is objective information acquired in a process of mutual communication. Accordingly, it is possible to perform more accurate inference, as compared with a case of inferring the element necessary for relationship building with the partner on the basis of the action history of the partner, and preference information and attribute information about the partner. This consequently makes it possible to more accurately determine mutual congeniality.

7. Modification Examples of Respective Embodiments

In the first embodiment described above and the modification examples thereof, for example, the electronic apparatus 10 may include a vibration signal generator 21*a* and a vibration section 21*b*, as illustrated in FIG. 9. In addition, in the second embodiment described above, for example, the electronic apparatus 40 may include the vibration signal generator 21*a* and the vibration section 21*b*, as illustrated in FIG. 10. In addition, in the third embodiment described above, for example, each of the devices 310 may include the vibration signal generator 21*a* and the vibration section 21*b*, as illustrated in FIG. 11.

The vibration signal generator 21*a* generates a vibration signal for outputting vibration data inputted from the signal processor 15, and outputs the vibration signal to the vibration section 21*b*. The vibration section 21*b* vibrates on the basis of the vibration signal inputted from the vibration signal generator 21*a*. The signal processor 15 may generate vibration data on the basis of, for example, at least one of the voice context 16*d* (voice data), the non-voice context 16*d* (data of the line of sight), or the emotional information 16*c*. In this case, the vibration section 21*b* vibrates on the basis of, for example, at least one of the voice context 16*d* (voice data), the non-voice context 16*d* (data of the line of sight), or the emotional information 16*c*. In such a case, the user is able to infer the element necessary for relationship building with the partner from vibration by the vibration section 21*b*. This consequently makes it possible to more accurately determine mutual congeniality.

It is to be noted that, in the third embodiment described above and the modification examples thereof, the user input receiver 14 may be provided for each device 310. In such a case, the user is able to input information from the device 310 with use of the user input receiver 14. As a result, even in a case where each device 310 is, for example, a mobile device such as a smartphone and the user carries the device 310, it is possible to input information for each device 310.

In the first embodiment described above and the modification examples thereof, the plurality of electronic apparatuses 10 may be coupled to each other by means other than the network 30.

Modification Example G

In the first to third embodiments described above and the modification examples thereof, the biological sensor 20 may be mounted in a head-mounted display (HMD) 400, for example, as illustrated in FIG. 22. In the head-mounted display 400, for example, a detection electrode 403 of the biological sensor 20 may be provided on an inner surface or the like of each of a pad part 401 and a band part 402.

In addition, in the first to third embodiments described above and the modification examples thereof, the biological sensor 20 may be mounted, for example, in a head band 500 as illustrated in FIG. 23. In the head band 500, for example, a detection electrode 503 of the biological sensor 20 may be provided on an inner surface or the like of each of band parts 501 and 502 to be in contact with the head.

In addition, in the first to third embodiments described above and the modification examples thereof, the biological sensor 20 may be mounted, for example, in a headphone 600 as illustrated in FIG. 24. In the headphone 600, for example, a detection electrode 603 of the biological sensor 20 may be provided on an inner surface of a band part 601, an ear pad 602, or the like to be in contact with the head.

In addition, in the first to third embodiments described above and the modification examples thereof, the biological sensor 20 may be mounted, for example, in an earphone 700 as illustrated in FIG. 25. In the earphone 700, for example, a detection electrode 702 of the biological sensor 20 may be provided in an ear piece 701 to be inserted into the ear.

In addition, in the first to third embodiments described above and the modification examples thereof, the biological sensor 20 may be mounted, for example, in a watch 800 as illustrated in FIG. 26. In the watch 800, for example, a detection electrode 804 of the biological sensor 20 may be provided on an inner surface of a display part 801 that displays time or the like, an inner surface of a band part 802 (e.g., an inner surface of a buckle part 803), or the like.

In addition, in the first to third embodiments described above and the modification examples thereof, the biological sensor 20 may be mounted, for example, in glasses 900 as illustrated in FIG. 27. In the glasses 900, for example, a detection electrode 902 of the biological sensor 20 may be provided on an inner surface of a temple 901 or the like.

In addition, in the first to third embodiments described above and the modification examples thereof, the biological sensor 20 may also be mounted, for example, in a glove, a ring, a pencil, a pen, a controller of a game machine, or the like.

Modification Example H

In the first to third embodiments described above and the modification examples thereof, the signal processor 15 may derive, for example, feature amounts as given below, on the basis of electric signals of a pulse wave, an electrocardiogram, and a blood flow of a person to be evaluated obtained by a sensor, and may derive the arousal level 24e of the person to be evaluated, on the basis of the derived feature amounts.

(Pulse Wave, Electrocardiogram, and Blood Flow)

It is possible to derive the arousal level 24e of the person to be evaluated by using, for example, feature amounts as given below, which are obtained on the basis of electric signals of a pulse wave, an electrocardiogram, and a blood flow obtained by the sensor.

Heart rate per 1 s

Average value of heart rates per 1 s within a predetermined period (window)

rmssd (root mean square successive difference): root mean square of successive heartbeat intervals pnn50 (percentage of adjacent normal-to-normal intervals): percentage of the number of successive heartbeat intervals exceeding 50 ms LF: area of PSD of heartbeat intervals between 0.04 Hz and 0.15 Hz HF: area of PSD of heartbeat intervals between 0.15 Hz and 0.4 Hz

LF/(LF+HF)

HF/(LF+HF)

LF/HF

Heart rate entropy

SD1: standard deviation of Poincare plot (scatter diagram with an x-axis for t-th heartbeat interval and a y-axis for t+1-th heartbeat interval) in a direction of an axis of y=x SD2: standard deviation of Poincare plot in a direction of an axis perpendicular to y=x SD1/SD2

SDRR (standard deviation of RR interval): standard deviation of heartbeat interval In addition, in the first to third embodiments described above and the modification examples thereof, the signal processor 15 may derive, for example, feature amounts as given below, on the basis of electric signals (EDA: electrodermal activity) of emotional sweating of the person to be evaluated obtained by the sensor, and may derive the arousal level 24e of the person to be evaluated, on the basis of the derived feature amounts.

(Emotional Sweating)

It is possible to derive the arousal level 24e of the person to be evaluated by using the feature amounts as given below, which are obtained on the basis of electric signals of emotional sweating obtained by the sensor.

Number of SCRs (skin conductance response) occurring per minute

Amplitude of SCR

Value of SCL (skin conductance level)

Rate of change of SCL

For example, it is possible to separate SCR and SCL from EDA by using a method described in the following literature:

Benedek, M., & Kaernbach, C. (2010). A continuous measure of phasic electrodermal activity. Journal of neuroscience methods, 190(1), 80-91.

It is to be noted that, in derivation of the arousal level 24e, a single modal (one physiological index) may be used, or a combination of a plurality of modals (a plurality of physiological indices) may be used.

The signal processor 15 derives the feature amounts described above by using, for example, regression formulae illustrated in FIGS. 28 to 35 to be described later.

FIG. 28 illustrates an example of a relationship between a task difference Δha [%] and the accuracy rate R [%]. The task difference Δha [%] is a task difference in the pnn50 of a pulse wave between the time of solving the high difficulty level questions and the time of solving the low difficulty level questions. The accuracy rate R [%] is the accuracy rate at the time of solving the high difficulty level questions. The task difference Δha is a vector volume obtained by subtracting the pnn50 of the pulse wave at the time of solving the low difficulty level questions from the pnn50 of the pulse wave at the time of solving the high difficulty level questions. In FIG. 28, data for respective users are plotted, and features of the entirety of users are represented by a regression formula (regression line). In FIG. 28, the regression formula is represented by R=a10×Δha+b10.

A small task difference Δha in the pnn50 of the pulse wave means that the difference in the pnn50 of the pulse wave between the time of solving the high difficulty level questions and the time of solving the low difficulty level questions is small. It can be said that a user who has obtained such a result has a tendency in which, as the difficulty level of the questions becomes high, a task difference in the pnn50 of the pulse wave becomes smaller as compared with other users. Meanwhile, a large task difference Δha in the pnn50 of the pulse wave means that the difference in the pnn50 of the pulse wave between the time of solving the high difficulty level questions and the time of solving the low difficulty level questions is large. It can be said that a user who has obtained such a result has a tendency in which, as the difficulty level of the questions becomes high, the task difference in the pnn50 of the pulse wave becomes larger as compared with other users.

It is appreciated from FIG. 28 that, when the task difference Δha in the pnn50 of the pulse wave is large, the accuracy rate R for questions becomes high, and that, when the task difference Δha in the pnn50 of the pulse wave is small, the accuracy rate R for questions becomes small. It is appreciated from the above that a person who has large pnn50 of the pulse wave for difficult questions tends to have a high accuracy rate R (i.e., be able to answer accurately even for difficult questions to the same degree as for simple questions). Conversely, it is appreciated that a person who has small pnn50 of the pulse wave even for difficult questions tends to have a low accuracy rate R (i.e., the accuracy rate for the difficult questions is lowered).

Herein, as described above, it can be seen from FIG. 21 that, when the accuracy rate is high, the arousal level is low, and when the accuracy rate is low, the arousal level is high. It can be inferred from the above that, when the task difference Δha in the pnn50 of the pulse wave is large, the arousal level of the user is lower than the predetermined standard. in addition, it can be inferred that, when the task difference Δha in the pnn50 of the pulse wave is small, the arousal level of the user is higher than the predetermined standard.

It is appreciated from the above that using the task difference Δha in the pnn50 of the pulse wave and the regression formulae in FIGS. 21 and 28 makes it possible to derive the arousal level of the user.

FIG. 29 illustrates an example of a relationship between a task difference Δhb [%] and the accuracy rate R [%]. The task difference Δhb [%] is a task difference in dispersion of the pnn50 of the pulse wave between the time of solving the high difficulty level questions and the time of solving the low difficulty level questions. The accuracy rate R [%] is the accuracy rate at the time of solving the high difficulty level questions. The task difference Δhb is a vector volume obtained by subtracting the dispersion of the pnn50 of the pulse wave at the time of solving the low difficulty level questions from the dispersion of the pnn50 of the pulse wave at the time of solving the high difficulty level questions. In FIG. 29, data for respective users are plotted, and features of the entirety of users are represented by a regression formula (regression line). In FIG. 29, the regression formula is represented by R=a11×Δhb+b11.

A small task difference Δhb in the dispersion of the pnn50 of the pulse wave means that the difference in the dispersion of the pnn50 of the pulse wave between the time of solving the high difficulty level questions and the time of solving the low difficulty level questions is small. It can be said that a user who has obtained such a result has a tendency in which, as the difficulty level of the questions becomes high, the task difference in the dispersion of the pnn50 of the pulse wave becomes smaller as compared with other users. Meanwhile, a large task difference Δhb in the dispersion of the pnn50 of the pulse wave means that the difference in the dispersion of the pnn50 of the pulse wave between the time of solving the high difficulty level questions and the time of solving the low difficulty level questions is large. It can be said that a user who has obtained such a result has a tendency in which, as the difficulty level of the questions becomes high, the task difference in the dispersion of the pnn50 of the pulse wave becomes larger as compared with other users.

It is appreciated from FIG. 29 that, when the task difference Δhb in the dispersion of the pnn50 of the pulse wave is large, the accuracy rate R for questions becomes high, and that, when the task difference Δhb in the dispersion of the pnn50 of the pulse wave is small, the accuracy rate R for questions becomes small. It is appreciated from the above that a person who has large dispersion of the pnn50 of the pulse wave for difficult questions tends to have a high accuracy rate R (i.e., be able to answer accurately even for difficult questions to the same degree as for simple questions). Conversely, it is appreciated that a person who has small dispersion of the pnn50 of the pulse wave even for difficult questions tends to have a low accuracy rate R (i.e., the accuracy rate for the difficult questions is lowered).

Herein, as described above, it can be seen from FIG. 21 that, when the accuracy rate is high, the arousal level is low, and when the accuracy rate is low, the arousal level is high. It can be inferred from the above that, when the task difference Δhb in the dispersion of the pnn50 of the pulse wave is large, the arousal level of the user is lower than the predetermined standard. In addition, it can be inferred that, when the task difference Δha in the dispersion of the pnn50 of the pulse wave is small, the arousal level of the user is higher than the predetermined standard.

It is appreciated from the above that using the task difference Δhb in the dispersion of the pnn50 of the pulse wave and the regression formulae in FIGS. 21 and 29 makes it possible to derive the arousal level of the user.

FIG. 30 illustrates an example of a relationship between a task difference Δhc [$ms^{-2}$ Hz] and the accuracy rate R [%]. The task difference Δhc [$ms^{-2}$ Hz] is a task difference in power in a low-frequency band (around 0.01 Hz) of a power spectrum obtained by performing FFT on the pnn50 of the pulse wave between the time of solving the high difficulty level questions and the time of solving the low difficulty level questions. The accuracy rate R [%] is the accuracy rate at the time of solving the high difficulty level questions. Hereinafter, the "power in a low-frequency band (around 0.01 Hz) of a power spectrum obtained by performing FFT on the pnn50 of the pulse wave" is referred to as "power in the low-frequency band of the pnn50 of the pulse wave". The task difference Δhc is a vector volume obtained by subtracting the power in the low-frequency band of the pnn50 of the pulse wave at the time of solving the low difficulty level questions from the power in the low-frequency band of the pnn50 of the pulse wave at the time of solving the high difficulty level questions. In FIG. 30, data for respective users are plotted, and features of the entirety of users are represented by a regression formula (regression line). In FIG. 30, the regression formula is represented by R=a12×Δhc+b12.

A large task difference Δhc in the power in the low-frequency band of the pnn50 of the pulse wave means that the difference in the power in the low-frequency band of the pnn50 of the pulse wave between the time of solving the high difficulty level questions and the time of solving the low difficulty level questions is large. It can be said that a user who has obtained such a result has a tendency in which, when solving the high difficulty level questions, the task difference in the power in the low-frequency band of the pnn50 of the pulse wave becomes larger as compared with other users. Meanwhile, a small task difference Δhc in the power in the low-frequency band of the pnn50 of the pulse wave means that the difference in the power in the low-frequency band of the pnn50 of the pulse wave between the time of solving the high difficulty level questions and the time of solving the low difficulty level questions is small. It can be said that a user who has obtained such a result has a tendency in which, as the difficulty level of the questions becomes high, the task difference in the power in the low-frequency band of the pnn50 of the pulse wave becomes smaller as compared with other users.

It is appreciated from FIG. 30 that, when the task difference Δhc in the power in the low-frequency band of the pnn50 of the pulse wave is large, the accuracy rate R for questions becomes high, and that, when the task difference Δhc in the power in the low-frequency band of the pnn50 of the pulse wave is small, the accuracy rate R for questions becomes low. It is appreciated from the above that a person who has large power in the low-frequency band of the pnn50 of the pulse wave even for difficult questions tends to have a high accuracy rate R (i.e., be able to answer accurately even for difficult questions to the same degree as for simple questions). Conversely, it is appreciated that a person who has small power in the low-frequency band of the pnn50 of the pulse wave for difficult questions tends to have a low accuracy rate R (i.e., the accuracy rate for the difficult questions is lowered).

Herein, as described above, it can be seen from FIG. 21 that, when the accuracy rate is high, the arousal level is low, and when the accuracy rate is low, the arousal level is high. It can be inferred from the above that, when task difference $\Delta hc$ in the power in the low-frequency band of the pnn50 of the pulse wave is small, the arousal level of the user is lower than the predetermined standard. In addition, it can be inferred that, when the task difference $\Delta hc$ in the power in the low-frequency band of the pnn50 of the pulse wave is large, the arousal level of the user is higher than predetermined standard.

It is appreciated from the above that using the task difference $\Delta hc$ in the power in the low-frequency band of the pnn50 of the pulse wave and the regression formulae in FIGS. 21 and 30 makes it possible to derive the arousal level of the user.

FIG. 31 illustrates an example of a relationship between a task difference $\Delta hd$ [ms] and the accuracy rate R [%]. The task difference $\Delta hd$ [ms] is a task difference in the rmssd of the pulse wave between the time of solving the high difficulty level questions and the time of solving the low difficulty level questions. The accuracy rate R [%] is the accuracy rate at the time of solving the high difficulty level questions. The task difference $\Delta hd$ is a vector volume obtained by subtracting the rmssd of the pulse wave at the time of solving the low difficulty level questions from the rmssd of the pulse wave at the time of solving the high difficulty level questions. In FIG. 31, data for respective users are plotted, and features of the entirety of users are represented by a regression formula (regression line). In FIG. 31, the regression formula is represented by $R=a13\times\Delta hd+b13$.

A large task difference $\Delta hd$ in the rmssd of the pulse wave means that the difference in the rmssd of the pulse wave between the time of solving the high difficulty level questions and the time of solving the low difficulty level questions is large. It can be said that a user who has obtained such a result has a tendency in which, when solving the high difficulty level questions, the task difference in the rmssd of the pulse wave becomes larger as compared with other users. Meanwhile, a small task difference $\Delta hd$ in the rmssd of the pulse wave means that the difference in the rmssd of the pulse wave between the time of solving the high difficulty level questions and the time of solving the low difficulty level questions is small. It can be said that a user who has obtained such a result has a tendency in which, as the difficulty level of the questions becomes high, the task difference in the rmssd of the pulse wave becomes smaller as compared with other users.

It is appreciated from FIG. 31 that, when the task difference $\Delta hd$ in the rmssd of the pulse wave is large, the accuracy rate R for questions becomes high, and that, when the task difference $\Delta hd$ in the rmssd of the pulse wave is small, the accuracy rate R for questions becomes small. It is appreciated from the above that a person who has large rmssd of the pulse wave even for difficult questions tends to have a high accuracy rate R (i.e., be able to answer accurately even for difficult questions to the same degree as for simple questions). Conversely, it is appreciated that a person who has small rmssd of the pulse wave for difficult questions tends to have a low accuracy rate R (i.e., the accuracy rate for the difficult questions is lowered).

Herein, as described above, it can be seen from FIG. 21 that, when the accuracy rate is high, the arousal level is low, and when the accuracy rate is low, the arousal level is high. It can be inferred from the above that, when the task difference $\Delta hd$ in the rmssd of the pulse wave is small, the arousal level of the user is lower than the predetermined standard. In addition, it can be inferred that, when the task difference $\Delta hd$ in the rmssd of the pulse wave is large in a negative direction, the arousal level of the user is higher than the predetermined standard.

It is appreciated from the above that using the task difference $\Delta hd$ in the rmssd of the pulse wave and the regression formulae in FIGS. 21 and 31 makes it possible to derive the arousal level of the user.

FIG. 32 illustrates an example of a relationship between a task difference $\Delta he$ [ms] and the accuracy rate R [%]. The task difference $\Delta he$ [ms] is a task difference in dispersion of the rmssd of the pulse wave between the time of solving the high difficulty level questions and the time of solving the low difficulty level questions. The accuracy rate R [%] is the accuracy rate at the time of solving the high difficulty level questions. The task difference $\Delta he$ is a vector volume obtained by subtracting the dispersion of the rmssd of the pulse wave at the time of solving the low difficulty level questions from the dispersion of the rmssd of the pulse wave at the time of solving the high difficulty level questions. In FIG. 32, data for respective users are plotted, and features of the entirety of users are represented by a regression formula (regression line). In FIG. 32, the regression formula is represented by $R=a14\times\Delta he+b14$.

A large task difference $\Delta he$ in the dispersion of the rmssd of the pulse wave means that the difference in the dispersion of the rmssd of the pulse wave between the time of solving the high difficulty level questions and the time of solving the low difficulty level questions is large. It can be said that a user who has obtained such a result has a tendency in which, when solving the high difficulty level questions, the task difference in the dispersion of the rmssd of the pulse wave becomes larger as compared with other users. Meanwhile, a small task difference $\Delta he$ in the dispersion of the rmssd of the pulse wave means that the difference in the dispersion of the rmssd of the pulse wave between the time of solving the high difficulty level questions and the time of solving the low difficulty level questions is small. It can be said that a user who has obtained such a result has a tendency in which, as the difficulty level of the questions becomes high, the task difference in the dispersion of the rmssd of the pulse wave becomes smaller as compared with other users.

It is appreciated from FIG. 32 that, when the task difference $\Delta he$ in the dispersion of the rmssd of the pulse wave is large, the accuracy rate R for questions becomes high, and that, when the task difference $\Delta he$ in the dispersion of the rmssd of the pulse wave is small, the accuracy rate R for questions becomes small. It is appreciated from the above that a person who has large dispersion of the rmssd of the pulse wave even for difficult questions tends to have a high accuracy rate R (i.e., be able to answer accurately even for difficult questions to the same degree as for simple questions). Conversely, it is appreciated that a person who has small dispersion of the rmssd of the pulse wave for difficult questions tends to have a low accuracy rate R (i.e., the accuracy rate for the difficult questions is lowered).

Herein, as described above, it can be seen from FIG. 21 that, when the accuracy rate is high, the arousal level is low, and when the accuracy rate is low, the arousal level is high. It can be inferred from the above that, when the task difference $\Delta he$ in the dispersion of the rmssd of the pulse wave is small, the arousal level of the user is lower than the predetermined standard. In addition, it can be inferred that, when the task difference Δhe in the dispersion of the rmssd of the pulse wave is large in the negative direction, the arousal level of the user is higher than the predetermined standard.

It is appreciated from the above that using the task difference Δhe in the dispersion of the rmssd of the pulse wave and the regression formulae in FIGS. 21 and 32 makes it possible to derive the arousal level of the user.

FIG. 33 illustrates an example of a relationship between a task difference Δhf [$ms^2$/Hz] and the accuracy rate R [%]. The task difference Δhf [$ms^2$/Hz] is a task difference in power in a low-frequency band (around 0.01 Hz) of a power spectrum obtained by performing FFT on the rmssd of the pulse wave between the time of solving the high difficulty level questions and the time of solving the low difficulty level questions. The accuracy rate R [%] is the accuracy rate at the time of solving the high difficulty level questions. Hereinafter, the "power in a low-frequency band (around 0.01 Hz) of a power spectrum obtained by performing FFT on the rmssd of the pulse wave" is referred to as "power in the low-frequency band of the rmssd of the pulse wave". The task difference Δhf is a vector volume obtained by subtracting the power in the low-frequency band of the rmssd of the pulse wave at the time of solving the low difficulty level questions from the power in the low-frequency band of the rmssd of the pulse wave at the time of solving the high difficulty level questions. In FIG. 33, data for respective users are plotted, and features of the entirety of users are represented by a regression formula (regression line). In FIG. 33, the regression formula is represented by R=a15×Δhf+b15.

A large task difference Δhf in the power in the low-frequency band of the rmssd of the pulse wave means that the difference in the power in the low-frequency band of the rmssd of the pulse wave between the time of solving the high difficulty level questions and the time of solving the low difficulty level questions is large. It can be said that a user who has obtained such a result has a tendency in which, when solving the high difficulty level questions, the task difference in the power in the low-frequency band of the rmssd of the pulse wave becomes larger as compared with other users. Meanwhile, a small task difference Δhf in the power in the low-frequency band of the rmssd of the pulse wave means that the difference in the power in the low-frequency band of the rmssd of the pulse wave between the time of solving the high difficulty level questions and the time of solving the low difficulty level questions is small. It can be said that a user who has obtained such a result has a tendency in which, as the difficulty level of the questions becomes high, the task difference in the power in the low-frequency band of the rmssd of the pulse wave becomes smaller as compared with other users.

It is appreciated from FIG. 33 that, when the task difference Δhf in the power in the low-frequency band of the rmssd of the pulse wave is large, the accuracy rate R for questions becomes high, and that, when the task difference Δhf in the power in the low-frequency band of the rmssd of the pulse wave is small, the accuracy rate R for questions becomes small. It is appreciated from the above that a person who has large power in the low-frequency band of the rmssd of the pulse wave even for difficult questions tends to have a high accuracy rate R (i.e., be able to answer accurately even for difficult questions to the same degree as for simple questions). Conversely, it is appreciated that a person who has small power in the low-frequency band of the rmssd of the pulse wave for difficult questions tends to have a low accuracy rate R (i.e., the accuracy rate for the difficult questions is lowered).

Herein, as described above, it can be seen from FIG. 21 that, when the accuracy rate is high, the arousal level is low, and when the accuracy rate is low, the arousal level is high. It can be inferred from the above that, when the task difference Δhf in the power in the low-frequency band of the rmssd of the pulse wave is small, the arousal level of the user is lower than the predetermined standard. In addition, it can be inferred that, when the task difference Δhf in the power in the low-frequency band of the rmssd of the pulse wave is large in the negative direction, the arousal level of the user is higher than the predetermined standard.

It is appreciated from the above that using the task difference Δhf in the power in the low-frequency band of the rmssd of the pulse wave and the regression formulae in FIGS. 21 and 33 makes it possible to derive the arousal level of the user.

FIG. 34 illustrates an example of a relationship between a task difference Δhg [min] and the accuracy rate R [%]. The task difference Δhg [min] is a task difference in dispersion of the number of SCRs of the emotional sweating between the time of solving the high difficulty level questions and the time of solving the low difficulty level questions. The accuracy rate R [%] is the accuracy rate at the time of solving the high difficulty level questions. The task difference Δhg is a vector volume obtained by subtracting the dispersion of the number of the SCRs of the emotional sweating at the time of solving the low difficulty level questions from the dispersion of the number of SCRs of the emotional sweating at the time of solving the high difficulty level questions. In FIG. 34, data for respective users are plotted, and features of the entirety of users are represented by a regression formula (regression line). In FIG. 34, the regression formula is represented by R=a16×Δhg+b16.

A large task difference Δhg in the dispersion of the number of the SCRs of the emotional sweating means that the difference in the dispersion of the number of the SCRs of the emotional sweating between the time of solving the high difficulty level questions and the time of solving the low difficulty level questions is large. It can be said that a user who has obtained such a result has a tendency in which, when solving the high difficulty level questions, the task difference in the dispersion of the number of the SCRs of the emotional sweating becomes larger as compared with other users. Meanwhile, a small task difference Δhg in the dispersion of the number of the SCRs of the emotional sweating means that the difference in the dispersion of the number of the SCRs of the emotional sweating between the time of solving the high difficulty level questions and the time of solving the low difficulty level questions is small. It can be said that a user who has obtained such a result has a tendency in which, as the difficulty level of the questions becomes high, the task difference in the dispersion of the number of the SCRs of the emotional sweating becomes smaller as compared with other users.

It is appreciated from FIG. 34 that, when the task difference Δhg in the dispersion of the number of the SCRs of the emotional sweating is large, the accuracy rate R for questions becomes high, and that, when the task difference Δhg in the dispersion of the number of the SCRs of the emotional sweating is small, the accuracy rate R for questions becomes small. It is appreciated from the above that a person who has large dispersion of the number of the SCRs of the emotional sweating even for difficult questions tends to have a high accuracy rate R (i.e., be able to answer accurately even for difficult questions to the same degree as for simple questions). Conversely, it is appreciated that a person who has small dispersion of the number of the SCRs of the emotional sweating for difficult questions tends to have a low accuracy rate R (i.e., the accuracy rate for the difficult questions is lowered).

Herein, as described above, it can be seen from FIG. 21 that, when the accuracy rate is high, the arousal level is low, and when the accuracy rate is low, the arousal level is high. It can be inferred from the above that, when the task difference Δhg in the dispersion of the number of the SCRs of the emotional sweating is small, the arousal level of the user is lower than the predetermined standard. In addition, it can be inferred that, when the task difference Δhg in the dispersion of the number of the SCRs of the emotional sweating is large in the negative direction, the arousal level of the user is higher than the predetermined standard.

It is appreciated from the above that using the task difference Δhg in the dispersion of the number of the SCRs of the emotional sweating and the regression formulae in FIGS. 21 and 34 makes it possible to derive the arousal level of the user.

FIG. 35 illustrates an example of a relationship between a task difference Δhh [ms$^2$/Hz] and the accuracy rate R [%]. The task difference Δhh [ms$^2$/Hz] is a task difference in the number of the SCRs of the emotional sweating between the time of solving the high difficulty level questions and the time of solving the low difficulty level questions. The accuracy rate R [%] is the accuracy rate at the time of solving the high difficulty level questions. The task difference Δhh is a vector volume obtained by subtracting the number of the SCRs of the emotional sweating at the time of solving the low difficulty level questions from the number of SCRs of the emotional sweating at the time of solving the high difficulty level questions. In FIG. 35, data for respective users are plotted, and features of the entirety of users are represented by a regression formula (regression line). In FIG. 35, the regression formula is represented by R=a17×Δhh+b17.

A large task difference Δhh in the number of the SCRs of the emotional sweating means that the difference in the number of the SCRs of the emotional sweating between the time of solving the high difficulty level questions and the time of solving the low difficulty level questions is large. It can be said that a user who has obtained such a result has a tendency in which, when solving the high difficulty level questions, the task difference in the number of the SCRs of the emotional sweating becomes larger as compared with other users. Meanwhile, a small task difference Δhh in the number of the SCRs of the emotional sweating means that the difference in the number of the SCRs of the emotional sweating between the time of solving the high difficulty level questions and the time of solving the low difficulty level questions is small. It can be said that a user who has obtained such a result has a tendency in which, as the difficulty level of the questions becomes high, the task difference in the number of the SCRs of the emotional sweating becomes smaller as compared with other users.

It is appreciated from FIG. 35 that, when the task difference Δhh in the number of the SCRs of the emotional sweating is small, the accuracy rate R for questions becomes high, and that, when the task difference Δhh in the number of the SCRs of the emotional sweating is small, the accuracy rate R for questions becomes low. It is appreciated from the above that a person who has the large number of the SCRs of the emotional sweating even for difficult questions tends to have a high accuracy rate R (i.e., be able to answer accurately even for difficult questions to the same degree as for simple questions). Conversely, it is appreciated that a person who has the small number of the SCRs of the emotional sweating for difficult questions tends to have a low accuracy rate R (i.e., the accuracy rate for the difficult questions is lowered).

Herein, as described above, it can be seen from FIG. 21 that, when the accuracy rate is high, the arousal level is low, and when the accuracy rate is low, the arousal level is high. It can be inferred from the above that, when the task difference Δhh in the number of the SCRs of the emotional sweating is small, the arousal level of the user is lower than the predetermined standard. In addition, it can be inferred that, when the task difference Δhg in the number of the SCRs of the emotional sweating is large in the negative direction, the arousal level of the user is higher than the predetermined standard.

It is appreciated from the above that using the task difference Δhh in the number of the SCRs of the emotional sweating and the regression formulae in FIGS. 21 and 35 makes it possible to derive the arousal level of the user.

In addition, in the regression formula according to any of the first to third embodiments described above and the modification examples thereof, for example, as illustrated in FIG. 36, a task difference Δtv in a median value (median) of reaction times may be used in place of the task difference Δtv in the dispersion of the reaction times.

In addition, in the first to third embodiments described above and the modification examples thereof, the regression formula is not limited to a straight line (regression line), but may be a curve (regression curve), for example. The curve (regression curve) may be, for example, a quadratic function. The regression formula defining the relationship between the arousal level k [%] and the accuracy rate R [%] may be defined as a quadratic function (R=a×k2+bk+c), for example, as illustrated in FIG. 37.

In addition, the present disclosure may have the following configurations, for example.

(1)
  An information processing system including:
    an estimation section that estimates emotional information about a target living body on the basis of at least one of biological information or motion information about the target living body acquired by a sensor; and
    a display section that displays the emotional information on a display surface.

(2)
  The information processing system according to (1), further including an acquisition section that acquires a non-voice context in a sensing period by the sensor, in which
    the display section displays the emotional information and the context.

(3)
  The information processing system according to (2), further including an imaging section that obtains a moving image of a face of a user who visually recognizes display of the display section via a lens provided adjacent to the display surface, in which
    the display section displays the context at a position close to the lens on the display surface.

(4)
  The information processing system according to (1), further including an acquisition section that acquires a voice context in a sensing period by the sensor, in which
    the display section displays the emotional information and the context.

(5)

The information processing system according to any one of (1) to (4), in which the emotional information includes at least one of an arousal level or comfort/discomfort of the target living body.

(6)

The information processing system according to (4), in which the context includes information about conversation of the target living body.

(7)

The information processing system according to any one of (1) to (6), further including a vibration section that vibrates on the basis of the emotional information.

(8)

An information processing system including:
- a first estimation section that estimates emotional information about a first target living body on the basis of at least one of first biological information or first motion information about the first target living body acquired by a first sensor;
- a second estimation section that estimates emotional information about a second target living body on the basis of at least one of second biological information or second motion information about the second target living body acquired by a second sensor; and
- a display section that displays the emotional information acquired by the first estimation section and the emotional information acquired by the second estimation section together on a display surface.

(9)

The information processing system according to (8), further including an acquisition section that acquires a non-voice context in a sensing period by the first sensor and the second sensor, in which
the display section displays the emotional information acquired by the first estimation section, the emotional information acquired by the second estimation section, and the context acquired by the acquisition section together on the display surface.

(10)

The information processing system according to (9), in which
the first target living body includes a user who visually recognizes display of the display section, and
the second target living body includes a communication partner.

(11)

The information processing system according to (10), further including an imaging section that obtains a moving image of a face of the user via a lens provided adjacent to the display surface, in which
the display section displays the context at a position close to the lens on the display surface.

(12)

The information processing system according to (8), further including an acquisition section that acquires a voice context in a sensing period by the first sensor and the second sensor, in which
the display section displays the emotional information, and graphically displays the voice context.

(13)

The information processing system according to any one of (8) to (12), in which
the emotional information acquired by the first estimation section includes one of an arousal level and comfort/discomfort of the first target living body, and
the emotional information acquired by the second estimation section includes one of an arousal level and comfort/discomfort of the second target living body.

(14)

The information processing system according to any one of (8) to (13), in which the context includes information about at least one of at least one of motion or conversation of the first target living body, or at least one of motion or conversation of the second target living body.

(15)

An information processing system including:
- an estimation section that estimates emotional information about a target living body on the basis of at least one of biological information or motion information about the target living body acquired by a sensor;
- an acquisition section that acquires a context in a sensing period by the sensor; and
- an association section that associates the emotional information acquired by the estimation section and the context acquired by the acquisition section with each other.

(16)

The information processing system according to (15), in which
the context includes non-voice information, and
the information processing system further includes a display section that displays the emotional information and the context together on a display surface.

(17)

The information processing system according (15), in which
the context includes voice information,
the information processing system further includes and the information processing system further includes a display section that displays the emotional information and graphically displays the context.

(18)

An information processing system including:
- a first estimation section that estimates emotional information about a first target living body on the basis of at least one of first biological information or first motion information about the first target living body acquired by a first sensor;
- a second estimation section that estimates emotional information about a second target living body on the basis of at least one of second biological information or second motion information about the second target living body acquired by a second sensor;
- an acquisition section that acquires a context in a sensing period by the first sensor and the second sensor; and
- an association section that associates the emotional information acquired by the first estimation section, the emotional information acquired by the second estimation section, and the context acquired by the acquisition section in association with each other.

(19)

The information processing system according to (18), in which the information processing system further includes a display section that displays the emotional information acquired by the first estimation section, the emotional information acquired by the second estimation section, and the context together on a display surface.

In an information processing system according to a first aspect of the present disclosure, emotional information about a target living body is estimated on the basis of at least one of biological information or motion information about the target living body acquired by a sensor, and is displayed on a display surface. Accordingly, for example, in a case where the target living body is a communication partner, a user is able to infer an element necessary for relationship building with the partner on the basis of emotional information about the partner. Herein, the emotional information about the partner is objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. In addition, for example, in a case where the target living body is the user oneself, the user is able to infer the element necessary for relationship building with the partner on the basis of the emotional information about the user oneself Herein, the emotional information about the user oneself is objective information acquired in a process of mutual communication. Accordingly, it is possible to perform more accurate inference, as compared with a case of inferring the element necessary for relationship building with the partner on the basis of the action history of the partner, and preference information and attribute information about the partner. This consequently makes it possible to more accurately determine mutual congeniality.

In an information processing system according to a second aspect of the present disclosure, emotional information about a first target living body is estimated on the basis of at least one of first biological information or first motion information about the first target living body acquired by a first sensor. Furthermore, emotional information about a second target living body is estimated on the basis of at least one of second biological information or second motion information about the second target living body acquired by a second sensor. Then, the emotional information acquired by a first estimation section and the emotional information acquired by a second estimation section are displayed together on a display surface. Accordingly, for example, in a case where the first target living body is the user oneself and the second target living body is a communication partner, the user is able to infer the element necessary for relationship building with the partner on the basis of both the emotional information acquired by the first estimation section and the emotional information acquired by the second estimation section. Herein, both the emotional information acquired by the first estimation section and the emotional information acquired by the second estimation section are objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. This consequently makes it possible to more accurately determine mutual congeniality.

In an information processing system according to a third aspect of the present disclosure, emotional information about a target living body is estimated on the basis of at least one of biological information or motion information about the target living body acquired by a sensor. Furthermore, a context in a sensing period by the sensor is acquired. Then, the emotional information acquired by an estimation section and the context acquired by an acquisition section are associated with each other. Accordingly, for example, in a case where the target living body is a communication partner, a user is able to infer the element necessary for relationship building with the partner on the basis of emotional information about the partner. Herein, the emotional information about the partner is objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. In addition, for example, in a case where the target living body is the user oneself, the user is able to infer the element necessary for relationship building with the partner on the basis of the emotional information about the user oneself Herein, the emotional information about the user oneself is objective information acquired in a process of mutual communication. Accordingly, it is possible to perform more accurate inference, as compared with a case of inferring the element necessary for relationship building with the partner on the basis of the action history of the partner, and preference information and attribute information about the partner. This consequently makes it possible to more accurately determine mutual congeniality.

In an information processing system according to a fourth aspect of the present disclosure, emotional information about a first target living body is estimated on the basis of at least one of first biological information or first motion information about the first target living body acquired by a first sensor. Furthermore, emotional information about a second target living body is estimated on the basis of at least one of second biological information or second motion information about the second target living body acquired by a second sensor. Furthermore, a context in a sensing period by the first sensor and the second sensor is acquired. Then, the emotional information acquired by a first estimation section, the emotional information acquired by a second estimation section, and the context acquired by an acquisition section are associated with each other. Accordingly, for example, in a case where the first target living body is the user and the second target living body is a communication partner, the user is able to infer the element necessary for relationship building with the partner on the basis of both the emotional information acquired by the first estimation section and the emotional information acquired by the second estimation section. Herein, both the emotional information acquired by the first estimation section and the emotional information acquired by the second estimation section are objective information acquired in a process of mutual communication. Accordingly, it is possible to perform more accurate inference, as compared with a case of inferring the personality of the partner and the element necessary for relationship building on the basis of the action history of the partner, and preference information and attribute information about the partner. This consequently makes it possible to more accurately determine mutual congeniality.

This application claims the priority on the basis of Japanese Patent Application No. 2021-056032 filed on Mar. 29, 2021 and Japanese Patent Application No. 2021-132938 filed on Aug. 17, 2021 with Japan Patent Office, the entire contents of which are incorporated in this application by reference.

It should be understood by those skilled in the art that various modifications, combinations, sub-combinations, and alterations may occur depending on design requirements and other factors insofar as they are within the scope of the appended claims or the equivalents thereof.

The invention claimed is:

1. An information processing system, comprising:
a sensor configured to acquire at least one of biological information of a target living body or motion information of the target living body;
an estimation section configured to estimate emotional information of the target living body based on the at least one of the biological information or the motion information;
an imaging section that includes a lens,
wherein the imaging section is configured to acquire a moving image of a face of a user via the lens;
an acquisition section configured to acquire, based on the acquired moving image, a non-voice context in a sensing period of the imaging section; and
a display section configured to display;
the emotional information at a first position on a display surface of the display section, and
the non-voice context at a second position on the display surface, wherein
the second position is closer to the lens than the first position,
the lens is adjacent to the display surface, and
the displayed emotional information and the displayed non-voice context are visually recognizable by the user.

2. The information processing system according to claim 1, wherein
the acquisition section is further configured to acquire a voice context in a sensing period of the sensor, and
the display section is further configured to display the voice context.

3. The information processing system according to claim 1, wherein the emotional information comprises at least one of
an arousal level of the target living body, or
one of comfort of the target living body or discomfort of the target living body.

4. The information processing system according to claim 2, wherein the voice context comprises information about a conversation of the target living body.

5. The information processing system according to claim 1, further comprising a vibration section configured to vibrate based on the emotional information.

6. An information processing system, comprising:
a first sensor configured to acquire at least one of first biological information of a first target living body or first motion information of the first target living body;
a first estimation section configured to estimate emotional information of the first target living body based on the at least one of the first biological information or the first motion information;
a second sensor configured to acquire at least one of second biological information of a second target living body or second motion information of the second target living body;
a second estimation section configured to estimate emotional information of the second target living body based on the at least one of the second biological information or the second motion information; and
a display section configured to concurrently display the emotional information of the first target living body and the emotional information of the second target living body on a display surface of the display section.

7. The information processing system according to claim 6, further comprising an acquisition section configured to acquire a non-voice context in a sensing period of each of the first sensor and the second sensor,
wherein the display section is further configured to concurrently display the emotional information of the first target living body, the emotional information of the second target living body, and the non-voice context on the display surface.

8. The information processing system according to claim 7, wherein
the first target living body comprises a user who visually recognizes the emotional information of the first target living body, the emotional information of the second target living body, and the non-voice context displayed on the display section, and
the second target living body comprises a communication partner of the user.

9. The information processing system according to claim 8, further comprising an imaging section that comprises a lens adjacent to the display surface, wherein
the imaging section is configured to acquire a moving image of a face of the user via the lens, and
the display section is further configured to display the non-voice context at a position closer to the lens than the displayed emotional information of the first target living body.

10. The information processing system according to claim 6, further comprising an acquisition section configured to acquire a voice context in a sensing period of each of the first sensor and the second sensor, wherein
the display section is further configured to graphically display the voice context.

11. The information processing system according to claim 10, wherein the voice context comprises information about at least one of:
a motion of the first target living body,
a conversation of the first target living body,
a motion of the second target living body, or
a conversation of the second target living body.

12. The information processing system according to claim 6, wherein
the emotional information of the first target living body comprises at least one of
an arousal level of the first target living body, or
one of comfort of the first target living body or discomfort of the first target living body, and
the emotional information of the second target living body comprises at least one of
an arousal level of the second target living body, or
comfort of the second target living body or discomfort of the second target living body.

13. An information processing system, comprising:
a sensor configured to acquire at least one of biological information of a target living body or motion information of the target living body;
an estimation section configured to estimate emotional information of the target living body based on the at least one of the biological information or the motion information;
an acquisition section configured to acquire a context in a sensing period of the sensor; and
an association section configured to associate the emotional information with the context.

14. The information processing system according to claim 13, wherein
the context comprises non-voice information, and
the information processing system further comprises a display section configured to concurrently display the emotional information and the context on a display surface of the display section.

15. The information processing system according to claim 13, wherein
the context comprises voice information,
the information processing system further comprises a display section configured to:
display the emotional information; and
graphically display the context.

16. An information processing system, comprising:
a first sensor configured to acquire at least one of first biological information of a first target living body or first motion information of the first target living body;
a first estimation section configured to estimate emotional information of the first target living body based on the at least one of the first biological information or the first motion information;
a second sensor configured to acquire at least one of second biological information of a second target living body or second motion information of the second target living body;
a second estimation section configured to estimate emotional information of the second target living body based on at least one of the second biological information or the second motion information;
an acquisition section configured to acquire a context in a sensing period of each of the first sensor and the second sensor; and
an association section configured to associate the emotional information of the first target living body with each of the emotional information of the second target living body and the context.

17. The information processing system according to claim 16, wherein the information processing system further comprises a display section configured to concurrently display the emotional information of the first target living body, the emotional information of the second target living body, and the context on a display surface of the display section.

* * * * *